(12) United States Patent
Marchiano

(10) Patent No.: US 8,357,492 B2
(45) Date of Patent: Jan. 22, 2013

(54) DIGESTIVE SYSTEM CANCER STEM CELLS AND TESTS AND USES THEREFOR

(75) Inventor: Ruggero De Maria Marchiano, Rome (IT)

(73) Assignee: Istituto Superiore di Sanita, Rome (IT)

( * ) Notice: Subject to any disclaimer, the term of this patent is extended or adjusted under 35 U.S.C. 154(b) by 0 days.

(21) Appl. No.: 12/442,028

(22) PCT Filed: Sep. 19, 2007

(86) PCT No.: PCT/EP2007/008343
§ 371 (c)(1),
(2), (4) Date: Sep. 17, 2009

(87) PCT Pub. No.: WO2008/034645
PCT Pub. Date: Mar. 27, 2008

(65) Prior Publication Data
US 2010/0024049 A1 Jan. 28, 2010

(30) Foreign Application Priority Data
Sep. 19, 2006 (GB) ................................. 0618429.5

(51) Int. Cl.
*C12Q 1/68* (2006.01)
(52) U.S. Cl. ..................................... 435/6.13; 435/6.14
(58) Field of Classification Search ................. 435/6.13, 435/6.14
See application file for complete search history.

(56) References Cited

U.S. PATENT DOCUMENTS

| 2003/0119080 A1* | 6/2003 | Mangano ...................... 435/7.23 |
| 2005/0277162 A1* | 12/2005 | Gudas .......................... 435/7.23 |
| 2008/0132423 A1* | 6/2008 | Kondo ............................. 506/10 |
| 2010/0040637 A1* | 2/2010 | Van Orden et al. ......... 424/172.1 |

FOREIGN PATENT DOCUMENTS

WO    WO 2006/030473    3/2006

OTHER PUBLICATIONS

Burkert et al. Gastroenterology, 130(4), suppl.2, Abstract #T1658, 2006.*
Al-Hajj, M. et al. (2003) "Prospective identification of tumorigenic breast cancer cells," *Proc Natl. Acad. Sci. USA*, 100, 3983-8.
Bonnet, D et al. (1997) "Human acute myeloid leukemia is organized as a hierarchy that originates from a primitive hematopoietic cell," *Nat. Med.*, 3:730-7.
Chu, P. et al. (2000) "Cytokeratin 7 and cytokeratin 20 expression in epithelial neoplasms: a survey of 435 cases," *Mod. Pathol.*, 13: 962-72.
Clevers, H. (2005) "Stem cells, asymmetric division and cancer," *Nat. Genet.*, 37:1027-8.
Davidson, B. et al. (2002) "Detection of malignant epithelial cells in effusions using flow cytometric immunophenotyping: an analysis of 92 cases," *Am. J Clin. Pathol.*, 118, 85-92.
De Maria et al. (2007) "Identification and expansion of human colon-cancer-initiating cells," *Nature*, 445:11-115.
Dontu, G. et al. (2003) "In vitro propagation and transcriptional profiling of human mammary stem/progenitor cells," *Genes. Dev.*, 17, 1253-70.
Ee, H. C. et al. (1995) "Cdx-2 homeodomain protein expression in human and rat colorectal adenoma and carcinoma," *Am. J. Pathol.*, 147, 586-92.
Florek et al. (2005) "Prominin-1/CD133, a neural and hematopoietic stem cell marker, is expressed in adult human differentiated cells and certain types of kidney cancer," *Cell and Tissue Research*, vol. 319, No. 1, pp. 15-26.
Gannon, J.V. et al. (1990) "Activating mutations III p53 produce a common conformational effect. A monoclonal antibody specific for the mutant form," *EMBO. J.*, 9: 1595-602.
Haraguchi et al. (2006) "Characterization of a side population of cancer cells from human gastrointestinal system" *Stem Cells, Alphamed Press*, vol. 24, No. 3, pp. 506-513.
Jemal, A. et al. (2006) "Cancer statistics," *CA Cancer J. Clin.*, 56, 106-30.
Jessup, J. M. et al. (1988) "Growth potential of human colorectal carcinomas in nude mice: association with the preoperative serum concentration of carcinoembryonic antigen in patients," *Cancer Res.*, 48:1689-92.
Li et al. (2007) "Identification of pancreatic cancer stem cells," *Cancer Res.*, 67(3):1030-7.
Lin et al. (2007) "Elevated circulating endothelial progenitor marker CD133 messenger RNA levels predict colon cancer recurrence." *Cancer*, vol. 110, No. 3, pp. 534-542.
Ma et al. (2007) "Identification and Characterization of Tumourigenic Liver Cancer Stem/Progenitor Cells," *Gastroenterology*, 132 (7):2542-2556 17570225.
Moll, R. (1998) "Cytokeratins as markers of differentiation in the diagnosis of epithelial tumours," *Subcell Biochem* 31:205-62.
Norheim Andersen, S. et al. (1999) "Germline and somatic mutations in exon 15 of the APC gene and K-ras mutations in duodenal adenomas in patients with familial adenomatous polyposis," *Scand. J. Gastroenterol.*, 34:611-7.
O'Brien, Catherine et al. (2007) "A human colon cancer cell capable of initiating tumour growth in immunodeficient mice." Nature, vol. 445, No. 7123, pp. 106-110.
Pardal, R. et al. (2003) "Applying the principles of stem-cell biology to cancer," *Nat. Rev. Cancer.*, 3:895-902.
Powell, S. M. et al. "APC mutations occur early during colorectal Tumourigenesis," *Nature*, 359:235-7.
Prosser, J. et al. (1994) "APC mutation analysis by chemical cleavage of mismatch and a protein truncation assay in familial adenomatous polyposis," *Br. J. Cancer*, 70: 841-6.
Ricci-Vitiani et al. (2007) "Identification and expansion of human colon-cancer-initiating cells," Nature, vol. 445, No. 7123, pp. 111-115.
Rodrigues, N. R. et al. (1990) "Mutations in colorectal cancer," *Proc. Natl. Acad. Sci. USA*, 87:7555-9.
Salven, P. et al. (2003) "VEGFR-3 and CD133 identify a population of CD34+ lymphatic/vascular endothelial precursor cells," *Blood*, 101:168-72.

(Continued)

*Primary Examiner* — Thaian N Ton
(74) *Attorney, Agent, or Firm* — Greenlee Sullivan P.C.

(57) ABSTRACT

The CD133 marker has been found to be diagnostic of tumorigenic digestive system cancers, particularly malignant colorectal cancers. Tests to show such cells and uses for such cells are disclosed.

4 Claims, 9 Drawing Sheets

OTHER PUBLICATIONS

Sheahan, K. et al. (1990) "Differential reactivities of carcinoembryonic antigen (CEA) and CEA-related monoclonal and polyclonal antibodies in common epithelial malignancies," *Am. J. Clin. Pathol.*, 94:157-64.

Singh, S. K. et al. (2004) "Identification of human brain tumour initiating cells," *Nature*, 432:396-401.

Singh, S. K. et al. (2003) "Identification of a cancer stem cell in human brain tumours," *Cancer Res.*, 63, 5821-8.

Suetsugu et al. (2006) "Characterization of CD133<+> hepatocellular carcinoma cells as cancer stem/progenitor cells" *Biochemical and Biophysical Research Communications, Academic Press Inc.*, vol. 351, No. 4, pp. 820-824.

Uchida, N. et al. (2000) "Direct isolation of human central nervous system stem cells," *Proc. Natl. Acad. Sci. USA*, 97:14720-5.

Vescovi, A. L. et al. (1999) "Isolation and cloning of multipotential stem cells from the embryonic human CNS and establishment of transplantable human neural stem cell lines by epigenetic stimulation," *Exp. Neurol.*, 156, 71-83.

Wang, J. C. et al. (2005) "Cancer stem cells: lessons from leukemia," *Trends Cell Biol.*, 15:494-501.

Witek, M. E. et al . (2005) "The putative tumour suppressor Cdx2 is overexpressed by human colorectal adenocarcinomas," *Clin. Cancer Res.* 11:8549-56.

Yin, A. H. et al. (1997) "AC133, a novel marker for human hematopoietic stem and progenitor cells," *Blood*, 90:5002-12.

Examination Report, dated Dec. 9, 2011, for European patent application serial No. 07818427.2, corresponding to the present application, 9 pp.

Wei et al. (Dec. 2006) Database Medline No. NLM17345710, "Experimental Investigation of CD133 as a Putative Marker of Tumor-Initiating Cell in Laryngeal Carcinoma," 1 page.

Wei et al. (Sep. 2007) Database Medline No. NLM18051573, "Investigation of CD133 as Putative Marker of Tumor-Initiating Cell in Laryngeal Carcinoma," 1 page.

Zhou et al. (2007) "CD133, One of the Markers of Cancer Stem Cells in Hep-2 Cell Line," Laryngoscope 117:455-460.

\* cited by examiner

A

B

SEQUENCE LISTING

<160> NUMBER OF SEQ ID NOS: 15

<210> SEQ ID NO 1
<211> LENGTH: 865
<212> TYPE: PRT
<213> ORGANISM: Homo sapiens

<400> SEQUENCE: 1

```
Met Ala Leu Val Leu Gly Ser Leu Leu Leu Gly Leu Cys Gly Asn
1               5                   10                  15

Ser Phe Ser Gly Gly Gln Pro Ser Ser Thr Asp Ala Pro Lys Ala Trp
            20                  25                  30

Asn Tyr Glu Leu Pro Ala Thr Asn Tyr Glu Thr Gln Asp Ser His Lys
        35                  40                  45

Ala Gly Pro Ile Gly Ile Leu Phe Glu Leu Val His Ile Phe Leu Tyr
    50                  55                  60

Val Val Gln Pro Arg Asp Phe Pro Glu Asp Thr Leu Arg Lys Phe Leu
65              70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu Ala Gly Ile Ile Leu Cys
                100                 105                 110

Cys Val Leu Gly Leu Leu Phe Ile Ile Leu Met Pro Leu Val Gly Tyr
            115                 120                 125

Phe Phe Cys Met Cys Arg Cys Cys Asn Lys Cys Gly Gly Glu Met His
130                 135                 140

Gln Arg Gln Lys Glu Asn Gly Pro Phe Leu Arg Lys Cys Phe Ala Ile
145                 150                 155                 160

Ser Leu Leu Val Ile Cys Ile Ile Ser Ile Gly Ile Phe Tyr Gly
                165                 170                 175

Phe Val Ala Asn His Gln Val Arg Thr Arg Ile Lys Arg Ser Arg Lys
            180                 185                 190

Leu Ala Asp Ser Asn Phe Lys Asp Leu Arg Thr Leu Leu Asn Glu Thr
            195                 200                 205

Pro Glu Gln Ile Lys Tyr Ile Leu Ala Gln Tyr Asn Thr Thr Lys Asp
    210                 215                 220

Lys Ala Phe Thr Asp Leu Asn Ser Ile Asn Ser Val Leu Gly Gly Gly
225                 230                 235                 240

Ile Leu Asp Arg Leu Arg Pro Asn Ile Ile Pro Val Leu Asp Glu Ile
                245                 250                 255

Lys Ser Met Ala Thr Ala Ile Lys Glu Thr Lys Glu Ala Leu Glu Asn
                260                 265                 270

Met Asn Ser Thr Leu Lys Ser Leu His Gln Gln Ser Thr Gln Leu Ser
            275                 280                 285

Ser Ser Leu Thr Ser Val Lys Thr Ser Leu Arg Ser Ser Leu Asn Asp
            290                 295                 300

Pro Leu Cys Leu Val His Pro Ser Ser Glu Thr Cys Asn Ser Ile Arg
305                 310                 315                 320

Leu Ser Leu Ser Gln Leu Asn Ser Asn Pro Glu Leu Arg Gln Leu Pro
                325                 330                 335

Pro Val Asp Ala Glu Leu Asp Asn Val Asn Asn Val Leu Arg Thr Asp
            340                 345                 350

Leu Asp Gly Leu Val Gln Gln Gly Tyr Gln Ser Leu Asn Asp Ile Pro
        355                 360                 365

Asp Arg Val Gln Arg Gln Thr Thr Thr Val Val Ala Gly Ile Lys Arg
    370                 375                 380

Val Leu Asn Ser Ile Gly Ser Asp Ile Asp Asn Val Thr Gln Arg Leu
385                 390                 395                 400

Pro Ile Gln Asp Ile Leu Ser Ala Phe Ser Val Tyr Val Asn Asn Thr
                405                 410                 415
```

-continued

Glu Ser Tyr Ile His Arg Asn Leu Pro Thr Leu Glu Tyr Asp Ser
            420                 425             430

Tyr Trp Trp Leu Gly Gly Leu Val Ile Cys Ser Leu Leu Thr Leu Ile
        435                 440                 445

Val Ile Phe Tyr Tyr Leu Gly Leu Leu Cys Gly Val Cys Gly Tyr Asp
    450                 455                 460

Arg His Ala Thr Pro Thr Thr Arg Gly Cys Val Ser Asn Thr Gly Gly
465                 470                 475                 480

Val Phe Leu Met Val Gly Val Gly Leu Ser Phe Leu Phe Cys Trp Ile
                485                 490                 495

Leu Met Ile Ile Val Val Leu Thr Phe Val Phe Gly Ala Asn Val Glu
            500                 505                 510

Lys Leu Ile Cys Glu Pro Tyr Thr Ser Lys Glu Leu Phe Arg Val Leu
        515                 520                 525

Asp Thr Pro Tyr Leu Leu Asn Glu Asp Trp Glu Tyr Tyr Leu Ser Gly
    530                 535                 540

Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
                565                 570                 575

Asn Ser Phe Asn Ile Ser Glu His Leu Asn Ile Asn Glu His Thr Gly
            580                 585                 590

Ser Ile Ser Ser Glu Leu Glu Ser Leu Lys Val Asn Leu Asn Ile Phe
        595                 600                 605

Leu Leu Gly Ala Ala Gly Arg Lys Asn Leu Gln Asp Phe Ala Ala Cys
    610                 615                 620

Gly Ile Asp Arg Met Asn Tyr Asp Ser Tyr Leu Ala Gln Thr Gly Lys
625                 630                 635                 640

Ser Pro Ala Gly Val Asn Leu Leu Ser Phe Ala Tyr Asp Leu Glu Ala
                645                 650                 655

Lys Ala Asn Ser Leu Pro Pro Gly Asn Leu Arg Asn Ser Leu Lys Arg
            660                 665                 670

Asp Ala Gln Thr Ile Lys Thr Ile His Gln Arg Val Leu Pro Ile
        675                 680                 685

Glu Gln Ser Leu Ser Thr Leu Tyr Gln Ser Val Lys Ile Leu Gln Arg
    690                 695                 700

Thr Gly Asn Gly Leu Leu Glu Arg Val Thr Arg Ile Leu Ala Ser Leu
705                 710                 715                 720

Asp Phe Ala Gln Asn Phe Ile Thr Asn Thr Ser Ser Val Ile Ile
                725                 730                 735

Glu Glu Thr Lys Lys Tyr Gly Arg Thr Ile Ile Gly Tyr Phe Glu His
            740                 745                 750

Tyr Leu Gln Trp Ile Glu Phe Ser Ile Ser Glu Lys Val Ala Ser Cys
        755                 760                 765

Lys Pro Val Ala Thr Ala Leu Asp Thr Ala Val Asp Val Phe Leu Cys
    770                 775                 780

Ser Tyr Ile Ile Asp Pro Leu Asn Leu Phe Trp Phe Gly Ile Gly Lys
785                 790                 795                 800

Ala Thr Val Phe Leu Leu Pro Ala Leu Ile Phe Ala Val Lys Leu Ala
                805                 810                 815

Lys Tyr Tyr Arg Arg Met Asp Ser Glu Asp Val Tyr Asp Asp Val Glu
            820                 825                 830

Thr Ile Pro Met Lys Asn Met Glu Asn Gly Asn Asn Gly Tyr His Lys
        835                 840                 845

```
Asp His Val Tyr Gly Ile His Asn Pro Val Met Thr Ser Pro Ser Gln
    850                 855                 860
His
865
```

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
gcgtgatttc ccagaagata                                                  20

<210> SEQ ID NO 3
<211> LENGTH: 20
<212> TYPE: DNA
<213> ORGANISM: Artificial Sequence
<220> FEATURE:
<223> OTHER INFORMATION: PCR primer

<400> SEQUENCE: 3
ccccaggaca cagcatagaa                                                  20

<210> SEQ ID NO 4
<211> LENGTH: 19
<212> TYPE: DNA
<213> ORGANISM: Artificial Sequence
<220> FEATURE:
<223> OTHER INFORMATION: PCR primer

<400> SEQUENCE: 4
gctgccgtgt tccagttgc                                                   19

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
ccagccctgt cgtctctcca                                                  20

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
ggcctctgat tcctcactga                                                  20

<210> SEQ ID NO 7
<211> LENGTH: 20
<212> TYPE: DNA
<213> ORGANISM: Artificial Sequence
<220> FEATURE:
<223> OTHER INFORMATION: PCR primer

<400> SEQUENCE: 7
gccactgaca accacccctta                                                 20

```
<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
tgccacaggt ctccccaagg                                                     20

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9
agtgtgcagg gtggcaagtg                                                     20

<210> SEQ ID NO 10
<211> LENGTH: 20
<212> TYPE: DNA
<213> ORGANISM: Artificial Sequence
<220> FEATURE:
<223> OTHER INFORMATION: PCR primer

<400> SEQUENCE: 10
ccttactgcc tcttgcttct                                                     20

<210> SEQ ID NO 11
<211> LENGTH: 20
<212> TYPE: DNA
<213> ORGANISM: Artificial Sequence
<220> FEATURE:
<223> OTHER INFORMATION: PCR primer

<400> SEQUENCE: 11
ataactgcac ccttggtctc                                                     20

<210> SEQ ID NO 12
<211> LENGTH: 25
<212> TYPE: DNA
<213> ORGANISM: Artificial Sequence
<220> FEATURE:
<223> OTHER INFORMATION: PCR primer

<400> SEQUENCE: 12
ggataatttc agctgactaa acaga                                               25

<210> SEQ ID NO 13
<211> LENGTH: 25
<212> TYPE: DNA
<213> ORGANISM: Artificial Sequence
<220> FEATURE:
<223> OTHER INFORMATION: PCR primer

<400> SEQUENCE: 13
ttccgtttag ttaggtgcag ttatc                                               25

<210> SEQ ID NO 14
<211> LENGTH: 21
<212> TYPE: DNA
<213> ORGANISM: Artificial Sequence
<220> FEATURE:
<223> OTHER INFORMATION: PCR primer
```

```
<400> SEQUENCE: 14
ttacgtccat cgtggacagg a                                              21

<210> SEQ ID NO 15
<211> LENGTH: 20
<212> TYPE: DNA
<213> ORGANISM: Artificial Sequence
<220> FEATURE:
<223> OTHER INFORMATION: PCR primer

<400> SEQUENCE: 15
tgggctgggt gttagcctta                                                20
```

DIGESTIVE SYSTEM CANCER STEM CELLS AND TESTS AND USES THEREFOR

CROSS-REFERENCE TO RELATED APPLICATIONS

This application is the U.S. National Stage of International Application No. PCT/EP2007/008343, filed Sep. 19, 2007, which claims the benefit of Great Britain Patent Application No. 0618429.5, filed Sep. 19, 2006, both of which are hereby incorporated by reference to the extent not inconsistent with the disclosure hereof.

FIELD OF THE INVENTION

The present invention relates to testing for malignancy by assaying the presence of a cellular marker.

BACKGROUND

Cancers of the digestive system are very common and often fatal. For example, colon carcinoma is the second leading cause of cancer death'. Although there is increasing evidence that a rare population of undifferentiated cells is responsible for tumour formation and maintenance$^{2-4}$, such hypothesis has not been explored for colorectal or pancreatic cancers.

Surprisingly, it has now been established that the malignancy of colon cancers is driven by a very small percentage of the cells making up the cancer, and that these cells are characterised by the presence of the CD133 marker. Cells carrying the CD133 marker are referred to herein as CD133+ cells.

SUMMARY OF THE INVENTION

Thus in a first aspect, the present invention provides a test for malignancy in a digestive system tissue sample, particularly a gastrointestinal tract tissue sample, comprising assaying the sample for the presence of the CD133 marker.

We have now shown that tumorigenic cells in colon cancer are included in the CD133+ compartment, which accounts for about 2.5% of the tumour population. Subcutaneous injection of colon cancer CD133+ cells readily reproduced the original tumour in immunodeficient mice, while CD133− cells did not form any tumour. Such tumours were serially transplanted for several generations in which we progressively observed a faster growth without significant phenotypic alterations. Differently from CD133− cells, CD133+ colon cancer cells grew exponentially for more than one year in vitro as undifferentiated tumour spheres in serum-free medium containing epidermal growth factor (EGF) and fibroblast growth factor-2 (FGF-2), maintaining the ability to engraft and reproduce the same morphological and antigenic pattern of the original tumour. CD133+ tumour sphere cells differentiated upon cytokine removal and exposure to serum-containing medium, producing a progeny of non-tumorigenic cells very similar to the CD133− colon cancer population present in the original tumour. Thus, we have established that colorectal cancer is created and propagated by a small number of undifferentiated tumorigenic CD133+ cells, which should represent the preferential target of effective therapies.

It will be understood that the terms "digestive system, and "gastroenteric" or "gastroenterological can be used interchangeably. The alimentary canal and digestive glands regarded as an integrated system responsible for the ingestion, digestion, and absorption of food. This includes the mouth, tongue, pharynx, oesophagus, stomach, large and small intestines, liver, gallbladder, pancreas, spleen, bowel and colon. Therefore, it is preferred that the cancer being assayed for is at least one of the following: cancer of the mouth, cancer of the oesophagus, cancer of the stomach, cancer of the large or small intestine, cancer of the liver, cancer of the gallbladder, cancer of the pancreas, cancer of the spleen, cancer of the bowel and cancer of the colon.

Colon, colorectal, bowel and pancreatic cancers are particularly preferred.

More than one sample may be assayed for at one time, of course. The samples may be from different tissues. Suitable arrays may be used.

In a preferred embodiment, the test is for malignancy in a gastrointestinal tract tissue sample, and in that instance, it is preferred that the tissue samples may be taken from any part of the gastrointestinal tract, so that the test may be to ascertain the existence of a cancerous condition in the mouth, stomach or small intestine, for example, and cancers tested for may include oral, oesophageal, stomach, ileac, and colon cancers, for example. More specifically, it is particularly preferred that this test be used to determine the likelihood of existence of bowel cancer, and especially colon cancer.

Polyps can occur in the gastrointestinal tract, and particularly in the colon. However, many such polyps are benign, and may simply be removed by surgical means. What is important is to ascertain the existence of malignant cells in such polyps or other such gastrointestinal tissue as may be subject to the test of the invention.

For convenience, tissues and samples will generally be referred to herein as being from the colon, but it will be appreciated that reference to the colon includes reference to any other part of the digestive system or gastrointestinal tract, unless otherwise indicated, or apparent from the context.

By malignant is meant that attribute of cells in cancerous tissue that leads to the uncontrolled multiplication of undifferentiated cells. In the context of the present invention, it has been established that cells obtained from colon cancer tissue that do not express the CD133 marker are not capable of sustained existence beyond about two weeks, even under optimal conditions. By contrast, CD133+ cells are capable of replication under minimal conditions, and can readily generate new cancers in test animals.

The amount of cells in any given colon cancer that express the CD133 marker appears to be in the region of 2.5%, but this may be as low as 1% and as high as 5%, generally, and may vary beyond that under some circumstances.

In the tests of the invention, a positive reading for the presence of a cancerous condition may be set at a level of anything in excess of 1 in $10^3$, but may be refined lower to 1 in $10^4$, or even 1 in $10^5$, CD133+ cells in a sample.

While it is possible to test untreated samples, it is generally preferred to disrupt the samples so as to separate the individual cells in the sample. Although it is not critical to completely disrupt the sample, it is preferred that at least 10% of the cells of the treated sample are associated with no more than one other cell, and are more preferably not bound to any other cell. More preferably, this amount is 25%, and yet more preferably 50%. While it is desirable that amounts of in excess of 50% are not associated with other cells, it is also preferred that the individual cells be not further disrupted, especially where a cell counting technique is used. In one embodiment, the amount of cells specified is associated with no other cell.

Disruption of samples may be by any conventional technique, and may involve physical means, as well as biological and chemical means. Thus, a combination of grinding and enzymes may be sufficient.

It will also be appreciated that a test of the present invention may involve simply the detection of CD133, and this may comprise total disruption of the sample, with or without subsequent purification, and detection of a representative amount of CD133 in the sample. This will generally require a knowledge of the size of the sample and how much CD133 would normally be present in non-cancerous tissue.

The disruption may also be to a lesser level, such that the cellular contents are disrupted and removed, leaving intact membranes, or "ghosts", which may be labelled with anti-CD133 antibodies, for example, and subsequently counted.

Suitable antibodies are available and preferably recognise epitopes on the extracellular domain of CD133. The sequence of CD133 is available from the NCBI website, for instance under number NP_006008. This protein sequence is provided as SEQ ID NO.1. Thus, it is preferred that the test is capable of recognising this protein sequence or a sequence having at least 80%, more preferably at least 85%, more preferably at least 90%, more preferably at least 95%, more preferably at least 99%, more preferably at least 99.5%, and more preferably at least 99.9 sequence homology therewith, for instance using the BLAST program.

The amount of CD133+ cells that exist in normal colonic tissue is vanishingly small, to the extent that the detection of any cells whatsoever expressing CD133 is no small task even for the skilled person. Thus, merely establishing the presence of CD133+ cells by suitably labelled anti-CD133 antibodies will generally be indicative of a cancerous condition. The detection of cells expressing the CD133 marker may be by any suitable means, such as observation under a microscope, chromatography, FACS (fluorescence activated cellular selection) and flow cytometry, for example.

This process may be simplified such as by complete disruption of part of the sample and assaying for the presence of CD133 and, if CD133 is found, then employing more sophisticated techniques, such as FACS or flow cytometry, to ascertain the levels of CD133 marker expression in the remaining part of the sample.

The present invention further provides a method for establishing the presence of cancerous tissue in a sample from the gastrointestinal tract, comprising contacting the sample with an optionally labelled anti-CD133 antibody, and establishing the level of binding of the antibody to the sample.

The antibody may be labelled such as to fluoresce, or be prepared in the form of microbeads, or may be unlabelled but detectable on a chromatographic column, for example.

The present invention further provides a kit comprising said antibodies, together with instructions for the use thereof in the establishment of the existence of a cancerous condition, or otherwise.

We have also demonstrated that it is possible to obtain a virtually unlimited expansion of colon cancer tumourigenic cells. This may be used in in vitro and in vivo evaluation of drug efficacy. In this context, the use of xenografts carrying a neoplastic lesion that closely resembles the original tumour is probably more reliable than cell line-based xenografts, and is the preferred technique to be used in optimising individualised therapies.

Thus, the present invention further provides cultivating CD133+ digestive system or gastrointestinal tumour cells, and especially CD133+ colon carcinoma cells, under permissive conditions. Examples of suitable conditions are provided below and the De Maria paper (Nature 2007) described elsewhere, and in the present Examples.

The invention further provides the use of such cultivated cells to screen for therapeutic agents effective against cancers, especially those of the digestive system or gastrointestinal tract, and especially those tumours of whom the CD133+ cells form a part.

The present invention also provides a method of inducing a cancerous condition in an animal, preferably a mammalian model, preferably a mouse. Preferably, the animal is immunocompromised, an example of which is a SCID mouse. The invention therefore allows for a cancerous tissue, such as a pancreatic or colon cancer tissue expressing CD133, preferably a tumourigenic tissue, to be introduced into a model, such that the cancer is reproduced or re-created in that model. This significantly aids in the study of the cancer and effective treatments therefor, as described elsewhere.

In a further aspect, the invention also provides such an in vivo animal model, comprising a xenograft of CD133+ cells. The animal is preferably a mammal, preferably a mouse.

The model may also be a living tissue grown or maintained in vitro, such as tissue removed from an animal, or a tissue grown from suitable progenitor cells, such as stem cells.

It will also be appreciated that detection of the tumourigenic CD133+ cells before and after treatment will provide an indicator as to the nature of the treatment necessary, both with regard to intensity and duration, as well as selection of treatment. With this knowledge, the skilled physician will be able to modify or select treatment according to numbers of CD133+ cells present before and after treatment.

Thus, the present invention further provides selecting treatment for cancer of the digestive system or gastrointestinal tract according to the results obtained from a test of the invention.

Where reference is made herein to CD133, it will be appreciated that this relates not only to the protein, for instance that defined in SEQ ID NO. 1, but also a polynucleotide encoding said protein. Thus, assays may also be used that determine the presence of DNA or RNA encoding or leading to expression of the CD133 protein.

In one aspect, the present invention provides a method of screening therapeutic targets. This may be achieved by assaying for the presence of the CD133 protein or a polynucleotide encoding it.

The presence of CD133 is indicative of a tumourigenic population. Tumourigenic may be defined as capable of causing a cancerous condition, such as cell capable of initiating cancer or a cancer stem cell and thus becoming malignant or metastatic.

Also provided is a method for determining whether a sample or population of cells expresses, or is likely to express, a tumourigenic phenotype by assaying the sample for the presence of CD133. This may be by assaying for the presence of the CD133 protein or the presence of nucleotides encoding it.

In a further aspect, the invention provides a method for screening carcinogens comprising exposing a sample or population of cells to the carcinogen, for instance by contacting the cells with the carcinogen, and assaying the sample for the presence of the CD133 protein or the presence of nucleotides encoding it.

It will be appreciated that one of the advantages of the invention is that it allows one to detect cancer stem cells using the CD133 marker, and thus, characterize a sample or population as tumourigenic. Thus, we have now shown that it is possible to characterize a population as being tumourigenic (i.e. a cancer-initiating cell or a cancer stem cell) for diagnostic, prognostic and therapeutic purposes.

The following are just examples of how this may be achieved. Firstly, this may be achieved by in situ analysis, such as immunohistochemical techniques. For example, this may be achieved by using an antibody against CD133 in addition to other antibodies against survival or apoptosis-related factors (i.e. BCl-2 family proteins, IAP family proteins, caspases, protein kinases, for instance), or in combination with proteins involved in cell proliferation (i.e. Ki67, cyclins etc.) or any factor related to cell migration, metastatic features, therapeutic response and so forth.

Secondly, the characterization of a population as being tumourigenic may be achieved by analysing cells, preferably freshly purified cells, for the presence of CD133. In addition to CD133, it is also useful to assay for the presence of BerEP4+ cells (i.e. an assay for cells that are both CD133+/BerEP4+ cells. BerEP4 is also known as ESA and EpCAM. Expression of BerEP4 in CD133+ colon cancer stem cells is described in De Maria et al *Identification and expansion of human colon-cancer-initiating cells*; Nature Vol 445, 4 Jan. 2007, p 11-115); A third example of how the above characterisation may be achieved is by analysing CD133+ cells after in vitro or in vivo expansion (for instance colon cancer sphere cultures or colon cancer xenografts in immunocompromised mice).

The latter two examples are particularly useful for diagnostic, prognostic and therapeutic purposes, and for use in genomic, gene expression or proteomic arrays, for instance.

In other words, these assays can drive the therapy and help the discovery or testing of diagnostic, prognostic and therapeutic factors or procedures.

BRIEF DESCRIPTION OF THE DRAWINGS

FIG. 9A: Representative CD133 expression of tumor spheres from pancreatic carcinomas grown in serum-free medium in the presence of EGF and basic FGF. FIG. 9B: Tumourigenic activity of 50 spheres resuspended in Matrigel and injected subcutaneously in SCID mice. Data represent a typical experiment of three, using two pancreatic cancer stem cell lines obtained from two different patients.

FIG. 10A: Colon cancer xenografts reproducing lung cancer metastases are obtained by injection of CD133+ cells either in the tail vein or orthotopically in SCID mice. Arrows indicate colon cancer-like metastases in the lung parenchyma. FIG. 10B: Colon cancer xenografts reproducing spleen metastases are obtained by orthotopic injection of CD133+ cells. Arrows indicate colon cancer-like metastases in the spleen parenchyma. FIG. 10C: Colon cancer xenografts reproducing intraperitoneal metastases are obtained by orthotopic injection of CD133+ cells. Arrows indicate colon cancer-like metastases in the mouse peritoneum. FIG. 10D: Hematoxylin-eosin analysis showed a similar histological patterns between original tumor (human) and the mouse xenografts obtained after injection of CD133+ colon cancer cells.

DETAILED DESCRIPTION OF THE INVENTION

Stassi et al WO 2006/030473 describes a method for the purification and amplification of tumoural stem cells. The methods taught in Stassi et al can be used in the present invention as a useful means of selecting and growing the CD133+ cells. Accordingly, the disclosure is herein incorporated by reference, unless otherwise apparent. The disclosure relates to a method isolating/purifying and then amplifying "cancer stem cells." These can include colon and lung cancer cells (see page 8, line 29) for instance. There is nothing in this general disclosure of a CD133.

Li et al (Cancer Res. 2007 Feb. 1; 67(3):1030-7) mentioned below do disclose the existence of pancreatic cancer stem cells. However, they make no mention of CD133, but instead focus on a combination of three markers ESA+CD44+CD24+, which is a completely different population. Moreover, they were not able to generate cancer stem cell cultures, for instance by exponentially growing pancreatic cancer stem cells or pancreatic cancer spheres.

Instead, we have shown that the tumourigenic population in colon cancer is restricted to CD133+ cells, which are able to reproduce the original tumour in permissive recipients. Thus, colon undifferentiated cancer cells can be cultured and expanded in vitro as colon spheres in proliferative serum-free medium containing growth factors. This property is common to neural and epithelial stem and progenitor cells, which grow as spherical clusters that in the presence of serum or extracellular matrix differentiate upon growth factor removal[15-17].

To investigate whether CD133+ colon cancer cells display long-term tumourigenic potential, we evaluated the ability of these cells to generate tumours after serial transplantations. Tumour xenografts derived by the injection of freshly-isolated CD133+ cells were digested to isolate CD133+ and CD133− cells, which in turn were transplanted into secondary mice. Although the CD133− population contained a majority of human colon cancer cells, only unseparated and CD133+ cells were tumourigenic, whereas CD133− cells were not able to transfer the tumour in secondary mice (FIG. 4c), confirming the data obtained with cells directly isolated from the human tumour. Moreover, CD133+ tumour spheres obtained from similar CD133+-derived primary xenografts were subsequently transplanted into secondary mice whose tumours were used as a new source of CD133+ cells to generate tertiary and then quaternary tumours (Table 3). During the in vivo passages, CD133+ cells did not lose their tumourigenic potential but, rather, they increased their aggressiveness, as indicated by the faster growth and increasing number of CD133+CK20− cells of newly generated tumours (FIG. 4d-e).

Figure 4:
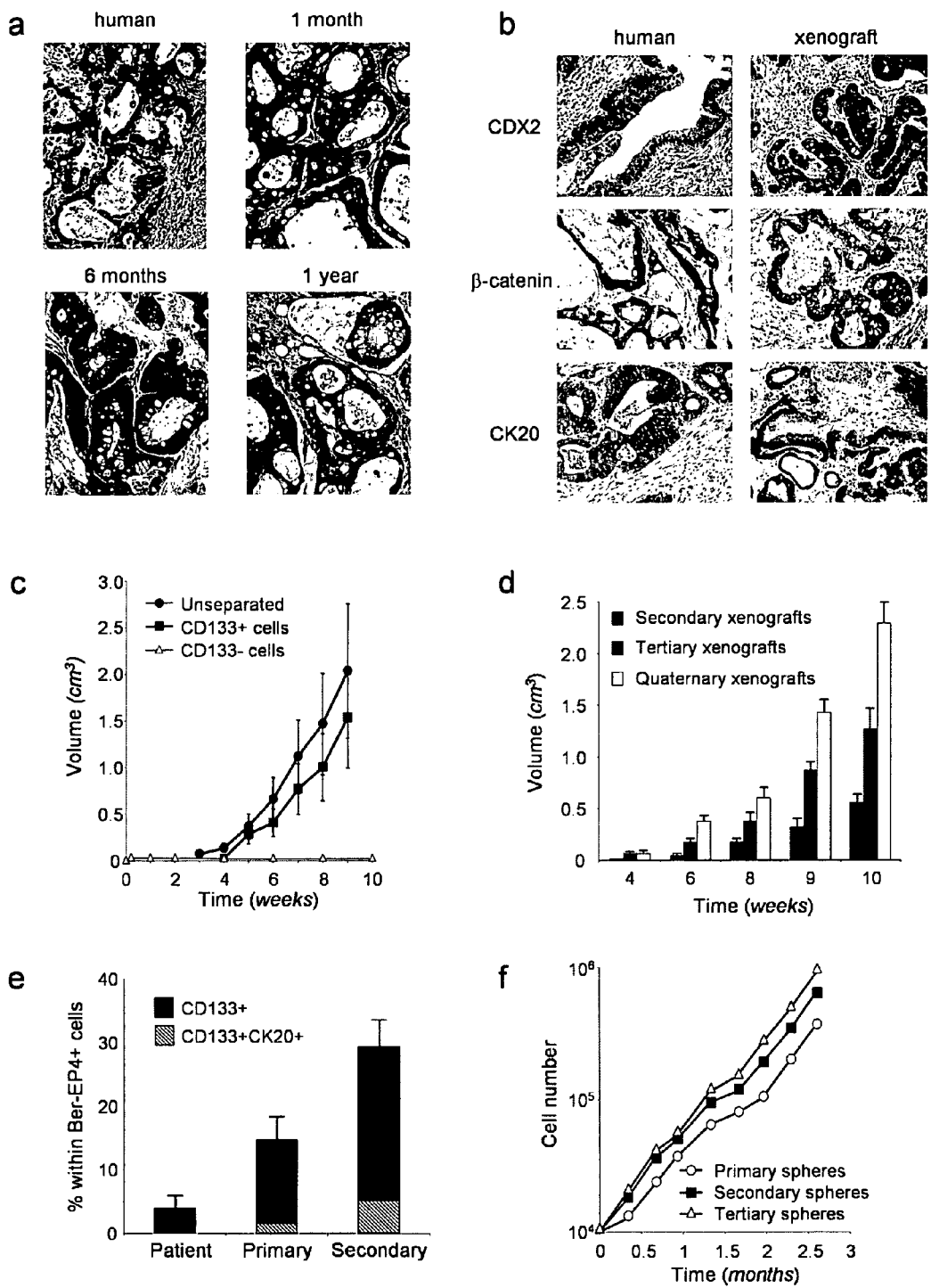
FIG. 4 shows that long-term tumorigenic potential of colon cancer CD133+ cells. a, Hematoxylin-Eosin analysis of original tumour (human) and mouse xenografts generated by spheres expanded in culture for the indicated times. b, Immunohistochemical analysis of the original tumour (human) and sphere-derived xenografts. c, Tumorigenic potential of $10^5$ CD133+, CD133− and total (unseparated) tumour cells purified from xenografts obtained in mice previously injected with freshly isolated CD133+ cells. d, Tumorigenic potential of colon cancer spheres derived by tumours induced by injection of 3,000 freshly isolated CD133+ cells (secondary xenografts), spheres derived by such secondary xenografts (tertiary xenografts) and spheres derived by tertiary xenografts (quaternary xenografts). Data are mean±s.d. of 3 different experiments. e, Percentage of CD133+ and CD133+ CK20+ cells among BerEp4+ cells from patient tumours and CD133+-derived primary and secondary xenografts. f, In vitro cell growth of colon cancer spheres obtained as indicated in e. A representative experiment of three is shown.

Accordingly, tumour spheres generated in vitro from these xenografts displayed an exponential growth that had the propensity to increase with serial xenografting (FIG. 4f). Thus, the CD133+ cell population resident in the colon tumour mass is able to generate serial xenografts showing a virtually unlimited growth potential.

We have also shown that introduction of tumour spheres containing colon cancer CD133+ cells into immunocompromised mice led to the reproduction of colon cancer metastases in the mice tissue. For instance, the introduction of CD133+ cells, originally isolated from colon cancer, as xenografts into the lungs of immunocompromised mice, led to the formation of colon-cancer metastases in the lung tissue. The same was also found in the spleen and peritoneum. This is particularly useful in the provision of in vivo mammalian models, such as mice, with xenograft metastases and the study of such cancers.

Thus, the present invention, as mentioned above, provides an animal model and a method of inducing a cancerous tissue, preferably a metastatic tissue, in an animal, comprising introducing CD133+ cells derived from a cancerous tissue. Preferably, the source of the CD133+ cells is heterologous to the animal recipient, such that a xenograft of tissue from a heterologous animal is introduced into the animal recipient or model. A preferred example is CD133+ cells from a human cancer transplanted or introduced into an animal model to form a xenograft, under suitable conditions. Preferably, the model is immunocompromised. Preferably the model is a mouse. Suitable conditions for xenografting or transplantation are described in the Examples or in the inventor's publication (De Maria et al Identification and expansion of human colon-cancer-initiating cells; Nature Vol 445, 4 Jan. 2007, p 11-115 and the supplementary examples provided online at Nature.com).

What was also surprising was that the CD133+ cells can be introduced both at the desired site by orthotopic injection, for instance, or by introduction into the blood, as was the case for the lung metastases.

The present invention will now be further illustrated with reference to the following, non-limiting Examples.

Example 1

CD133+ Cells are Colon Cancer Stem Cells and Markers for Colon Cancer

Methods
Cell Culture.

Colon adenocarcinoma samples were obtained from Sant'Andrea Hospital (Rome) upon patients' informed consent and approval by the local ethical committee. Surgical specimens were washed several times with phosphate buffered saline (PBS) and incubated overnight in DMEM-F12 containing 25 units/ml of penicillin, 25 µg/ml streptomycin and 10 µg/ml amphotericin B. Samples were subsequently subjected to mechanical and enzymatic dissociation. The resulting cancer cells were cultured in a NS-A basal serum-free medium (Euroclone, Irvine, UK), containing 2 mM L-glutamine, 0.6% glucose, 9.6 µg/ml putrescine, 6.3 ng/ml progesterone, 5.2 ng/ml sodium selenite, 0.025 mg/ml insulin, 0.1 mg/ml transferrin sodium salt (Sigma, St Louis, Mo.), and supplemented with 20 ng/ml EGF and 10 ng/ml FGF-2. To obtain primary tumour cell cultures, after enzymatic dissociation cells were plated on collagen-coated dishes in DMEM medium containing 10% FCS. Cultures of differentiated tumour cells were obtained from tumour spheres after growth factors removal and addition of 5% FCS. Endothelial cells were obtained by mechanical and enzymatic dissociation from a fragment of the human inferior thyroid vein.

Antibodies and Flow Cytometry. To characterise colon cancer stem cells, the following antibodies were used: anti-CD31-PE (clone WM-59, mouse $IgG_1$, BD Pharmingen); anti-CD45-PE (clone T29/33, mouse $IgG_1$, DakoCytomation); anti-Epithelial Antigen-FITC (clone Ber-EP4, mouse $IgG_1$, DakoCytomation); anti-Carcinoembryonic Antigen, CEA (polyclonal rabbit, DakoCytomation), anti-Cytokeratin 20 ($K_s$20.8, mouse $IgG_{2A}$, DakoCytomation) or isotype-matched control antibodies. FITC-conjugated anti-rabbit or anti-mouse secondary antibodies (Jackson ImmunoResearch Laboratories) were used where needed. Samples were analysed with FACSCan or LSR II flow cytometers (Becton Dickinson) and data were analysed with CELLQuest or Diva software (Becton Dickinson).

Magnetic and Cytofluorimetric Cell Separation.

For magnetic separation, cells were labelled 24-48 h after enzymatic dissociation with CD133/1 microbeads using the Miltenyi Biotec CD133 cell isolation kit. Alternatively, cells were labelled with CD133/1-PE antibody (Miltenyi Biotec) and sorted with a FACS Aria (Becton Dickinson). After magnetic or cytofluorimetric sorting, cell purity was evaluated by flow cytometry using CD133/2 (293C3)-PE or CD133/2 (293C3)-APC antibodies (Miltenyi Biotec).

Transplantation of cancer cells. After magnetic or cytofluorimetric cell sorting, $CD133^+$ and $CD133^-$ purified populations were resuspended in 100 µl of PBS and, before the injection, cell aliquots were diluted 1:1 with Growth Factor Reduced MATRIGEL Matrix (BD Biosciences). The injection was performed subcutaneously into the flank without anaesthesia. After 8-10 weeks mice were sacrificed by cervical dislocation, tumours were removed, fixed in 10% neutral buffered formalin solution (Sigma) and paraffin embedded.

Immunohistochemistry.

Immunohistochemistry was performed on formalin fixed paraffin embedded tissue, cell blocks or frozen tissue. Five p.m sections of paraffin embedded tissue and cell blocks were dewaxed in xylene and rehydrated with distilled water. Sections were then processed with the heat-induced epitope retrieval technique using a citrate buffer (0.01M pH6) followed by incubation with 3% hydrogen peroxide. The slides were subsequently incubated with the following antibodies for 1 hour at room temperature: CDX2 (BioGenex, clone CDX2-88, 1:100), CK20 (Dako, clone $K_s$20.8, 1:50), β-catenin (BD Transduction Laboratories, clone 14, 1:50). 5 p.m cryostat sections were acetone-fixed and incubated at room temperature with anti-human CD133/1 1:10 (Miltenyi Biotec, clone AC133). The reaction was performed using Elite Vector Stain ABC systems (Vector Laboratories) and DAB Substrate Chromogen (DakoCytomation) followed by haematoxylin counterstaining.

Real-Time PCR.

The relative quantification of CDX2 mRNA was performed by TaqMan technology, using the ABI PRISM 7900 DNA sequence detection system (Applied Biosystems). Commercial ready-to-use primers/probe mixes were used (Assay-on-Demand Gene Expression products, Hs00230919_m1; Applied Biosystems). CD133 mRNA relative quantification was performed by using SYBR® Green technology. CD133 specific primers were selected on the sequence NM_006017 (Gene Bank). The forward primer was GCGTGATTTCCCAGAAGATA (SEQ ID NO.2) and the reverse primer was CCCCAGGACACAGCATAGAA (SEQ ID NO.3), which produced an amplicon of 145 base pairs. Amplification was performed with 40 cycles of 15 seconds at 95° C. and 1 minute at 60° C. Human GAPDH was used as a housekeeping gene in both amplifications. Original input RNA amounts were calculated with a relative standard curve for CDX2 or CD133 and GAPDH RNA. Gene expression values were reported as the normalised percentage obtained by dividing the copy numbers of specific genes by GAPDH.

Supplementary Methods
Antibodies.

To isolate CD133− human cells from mouse xenografts anti-HLA-ABC (clone W6/32, mouse $IgG_{2a}$, DakoCytomation) antibody was used Immunofluorescence for p53 was performed on cytospin preparation of freshly purified CD133− cells, with anti-p53 (Pab240, mouse $IgG_1$, Calbiochem, Darmstadt, Germany) antibody specific for the conformational mutant form'.

Detection of p53 Mutations.

The analysis was performed on genomic DNA from CD133− tumor samples, which was extracted with PureLink™ Genomic DNA Purification Kit (Invitrogen S.R.L., Milan Italy) according to the manufacturer's protocol. The sequences analyzed corresponded to exons 5, 6, 7, and 8. Primer sequences were as follows:

```
exon 5
                                         (SEQ ID NO. 4)
forward, 5'-GCTGCCGTGTTCCAGTTGC-3',
and
                                         (SEQ ID NO. 5)
reverse, 5'-CCAGCCCTGTCGTCTCTCCA-3';

exon 6
                                         (SEQ ID NO. 6)
forward, 5'-GGCCTCTGATTCCTCACTGA-3'
and
```

```
                                                        (SEQ ID NO. 7)
reverse,  5'-GCCACTGACAACCACCCTTA-3';

exon 7
                                                        (SEQ ID NO. 8)
forward,  5'-TGCCACAGGTCTCCCCAAGG-3'
and
                                                        (SEQ ID NO. 9)
reverse,  5'-AGTGTGCAGGGTGGCAAGTG-3';

exon 8
                                                       (SEQ ID NO. 10)
forward,  5'-CCTTACTGCCTCTTGCTTCT-3'
and
                                                       (SEQ ID NO. 11)
reverse,  5'-ATAACTGCACCCTTGGTCTC-3'.
```

These primer sets defined PCR products of 293, 209,195, and 224 bp, respectively, which were used as template for sequencing reactions.

Protein Truncation Test (PTT) of APC.

Genomic DNA from normal and CD133− tumor samples was extracted with PureLink™ Genomic DNA Purification Kit (Invitrogen S.R.L., Milan Italy) according to the manufacturer's protocol. APC exon 15 was investigated by four overlapping PCR fragments[2]. PCR amplification was used to introduce the 17 by consensus T7 promoter sequence and a mammalian initiation sequence in-frame with a unique APC sequence. Genomic DNA was amplified by standard PCR conditions as previously described[3]. The PCR products were used in a TnT T7-coupled reticolocyte lysate system (Promega, Madison, Wis., USA) incorporating [355]-methionine in accordance with the manufacturer's instructions. The translation products were separated on 15% SDS-polyacrylamide gel in a vertical minigel apparatus (BioRad, Hercules, Calif., USA). Electrophoresis was performed until the bromophenol blue dye had run off the bottom of the gel. Gel was fixed, soaked in 10% glycerol, dried on a vacuum slab gel dryer and exposed to Kodak X-OMAT AR film overnight at −70° C.

Detection of murine cells in mouse xenografts. To verify the absence of contaminant mouse cells into the CD133− population of tumor cells isolated from mouse xenografts, genomic DNA was extracted from HLA-I/BerEp4 positive cells. Human alpha satellite and mouse myogenin expression was evaluated by PCR amplification. The following primers were used:

```
human alpha satellite forward,
                                                       (SEQ ID NO. 12)
5'-GGATAATTTCAGCTGACTAAACAGA-3',
and
reverse,
                                                       (SEQ ID NO. 13)
5'-TTCCGTTTAGTTAGGTGCAGTTATC-3';

mouse myogenin forward,
                                                       (SEQ ID NO. 14)
5'-TTACGTCCATCGTGGACAGGA-3',
and
reverse,
                                                       (SEQ ID NO. 15)
5'-TGGGCTGGGTGTTAGCCTTA-3'.
```

PCR was performed with 20 cycles for 30 seconds at 95° C., 30 seconds at 62° C., and 30 seconds at 72° C.

Results

Figure 1:
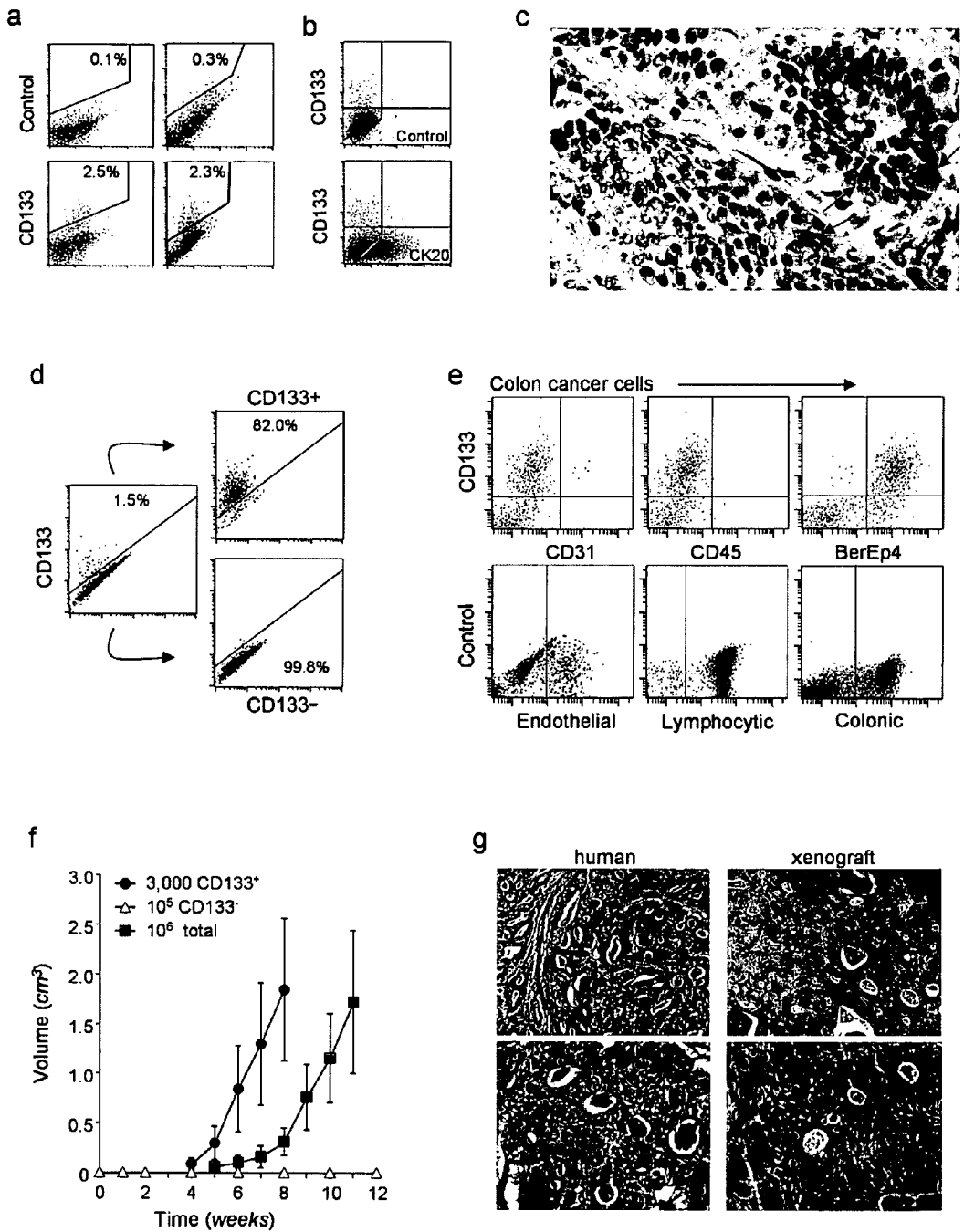
FIG. 1 shows that a rare CD133+ population of tumorigenic cells is present in colon cancer. a,b Flow cytometry analysis of CD133 expression as single staining (a) or in combination with CK20 (b) in freshly dissociated colon adenocarcinoma cells derived from three representative tumours. c, Immunohistochemical analysis of CD133 expression in colon cancer. Positive cells are brown and indicated by arrows. d, CD133 expression before (left) and after sorting of positive (right, top) and negative (right, bottom) colon cancer cells. e, Flow cytometry analysis of CD133, CD31, CD45 and Ber-EP4 expression in CD133− enriched colon cancer cells. Freshly-isolated normal endothelial, lymphocytic and colonic cells were used as positive controls. f, Evaluation of the tumorigenic potential of freshly-isolated $CD133^+$, $CD133^-$ and unseparated (total) colon cancer cells after subcutaneous injection in matrigel. Data concerning CD133+ and CD133− cells are mean±s.d. of 5 independent experiments in duplicate, referring to those tumours in which at least 1 out of 4 injections of $10^6$ unseparated cells were able to engraft. Data concerning unseparated cells are mean±s.d. of 11 successful engraftments out of 40 injections. g, Hematoxylin-eosin analysis with different (100×, top; 400×, bottom) original magnifications of colon cancer sections from the original tumour (human) and corresponding xenograft (xenograft) obtained after injection of CD133+ cells as in e.

Cancer neural stem cells can be identified and isolated through the presence of the CD133 marker, which is expressed by normal primitive cells of the neural, hematopoietic, epithelial and endothelial lineages[5-7]. To investigate the existence of a CD133+ cell population in colon cancer, we analysed by flow cytometry the immuno-phenotype of colonic tumour cells shortly after tissue dissociation. The vast majority of the samples analysed showed the presence of rare (2.5±1.4%) CD133+ cells (FIG. 1a and Table 2). These cells did not express cytokeratin 20 (CK20) (FIG. 1b), an intermediate filament protein whose presence is essentially restricted to differentiated cells from gastric and intestinal epithelium and urothelium[8]. To determine the anatomical location of CD133+ cells in colon cancer, we analysed by immunohistochemistry a number of colon cancer sections from six different patients. All the samples analysed showed similar results, with the presence of rare CD133+ cells in areas of high cellularity (FIG. 1c). CD133 expression in normal colon tissues was extremely infrequent as compared with the tumour counterpart, with CD133+ cells barely detectable upon extensive analysis of histological sections (data not shown).

Figure 5:
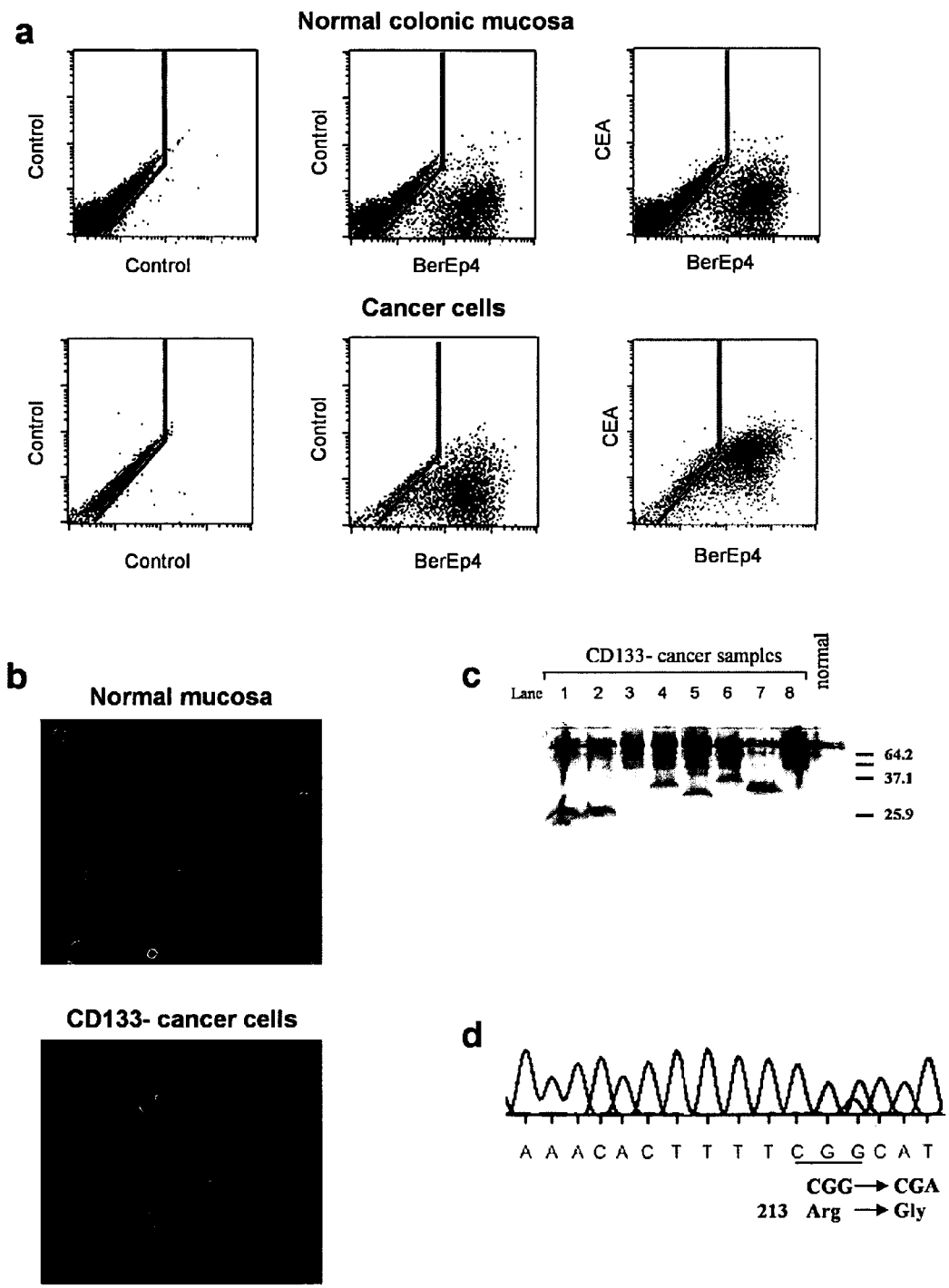
FIG. 5 shows that the CD133− population in colon cancer contains a considerable amount of cancer cells. a, Flow cytometry analysis of BerEP4 expression as single staining or in combination with CEA in freshly dissociated colon adenocarcinoma cells. b, Immunofluorescence analysis of mutant p53 (red) in cytospin preparations of CD133− colon cancer cells and control colonic mucosa cells. Nuclei are stained with Hoechst 33342 (blue). c, SDS-polyacrylamide gel electrophoresis analysis of protein truncation test products from APC fragment 15-2. Lanes 1-8 show DNA samples extracted from CD133− cancer cells, samples 1, 2, 4, 5, 6, 7 contain truncating mutations located at different positions along the fragment. The last lane shows a normal mucosa cell DNA sample (70 kDa). d, Genomic DNA from samples 3 and 8, which did not show any mutation in APC protein, was used for PCR amplification and sequencing of exons 5 to 8 of p53 gene. Figure shows the sequencing analysis of exon 6 of sample 3, point mutation consist in G/A substitution at codon 213.

The increased number of CD133+ cells in cancer samples may result from their oncogenic transformation. To evaluate the tumorigenic potential of colon CD133+ cells, we compared the ability of tumour-derived CD133+ and CD133− cells to engraft and give rise to subcutaneous tumours in severe combined immunodeficiency (SCID) mice. After surgical resection, colorectal cancer tissues were dissociated into single cells that were separated by immunomagnetic selection or flow cytometry on the basis of CD133 expression. This procedure resulted in a considerable enrichment of CD133+ cells (>80%) and an effective negative selection (>99.8%) of CD133− cells (FIG. 1d). The analysis of CD133− population revealed that a considerable amount (range 35-75%) of these cells displayed several features of cancers from the gastrointestinal tract, such as CarcinoEmbryonic Antigen (CEA)[9,10] expression and APC (adenomatous polyposis coli)" or p53 mutation[12], which were not present in normal colon epithelial cells (FIG. 5).

Before testing its in vivo oncogenic potential, we analysed the CD133+ population to evaluate the presence of hematopoietic and endothelial progenitors. CD133+ cells were negative for the pan-hematopoietic marker CD45, >97% positive for the epithelial marker Ber-EP4, and <2% represented by putative endothelial progenitors CD31+ (FIG. 1e). While $10^5$ CD133-colon cancer cells did not induce tumour formation, the injection of $10^6$ unseparated cells or 3,000 CD133+ cells resuspended in matrigel generated visible tumours after 4-5 weeks from the transplant (FIG. 10, indicating that colon cancer initiating cells are CD133+.

With the exception of Dukes stage A tumours, which reportedly are not tumorigenic in immunocompromised mice[13], we obtained engraftment with low numbers of CD133+ cells isolated from tumours of all the other stages (Table 1 and 2). Despite the high number of CD133+ cells present in $10^6$ unseparated cells, tumour formation following the injection of the total colon cancer population was slower and less efficient than that obtained with purified CD133+ cells (FIG. 1f and Table 2), in line with what was reported for breast cancer stem cells[14].

Figure 6:
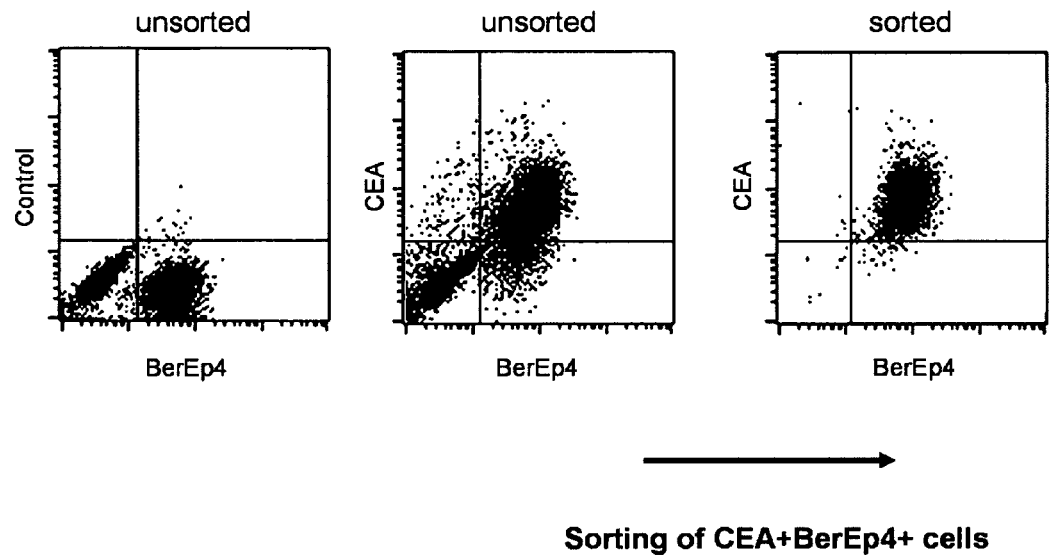
FIG. 6 shows the results of flow cytometry analysis of BerEp4 expression as single staining or in combination with CEA in freshly dissociated tissue specimens before (left and middle) and after sorting of double positive cells (right).

Moreover, hematoxylin-eosin staining and microscopical analysis indicated that CD133+-derived tumour xenografts consistently reproduced the primary tumour at histological level, including specific signature features infrequently observed in colorectal cancer, such as areas of eosinophilic secretions scattered in the neoplastic tissue (FIG. 1g). As expected, purified CD133-CEA+ colon cancer cells were unable to transfer the tumour in immunocompromised mice (FIG. 6 and Table 2).

Thus, the tumorigenic population in colon cancer is restricted to CD133+ cells, which are able to reproduce the original tumour in permissive recipients.

Normal and neoplastic stem cells from neural and epithelial organs can be expanded as sphere-like cellular clusters in serum-free medium containing EGF and FGF-2[4,14-17]. We cultivated the colonic cells obtained after dissociation of cancer tissues with such a proliferative medium for undifferentiated cells. After 4 weeks of culture, we obtained colon spheres formed by clusters of exponentially growing undifferentiated cells (FIG. 2a) from 4 out of 12 tumours (Table 3). Within ten passages, the doubling time of colon spheres was approximately ten days, which became less than 7 after 30 passages (FIG. 2b), as a likely consequence of a selection process. CD133− colon cancer cells invariably died in such serum-free conditions (Table 3 and data not shown), while being able to grow for about two weeks in serum-containing medium before gradually declining in number (FIG. 2b).

Figure 2:
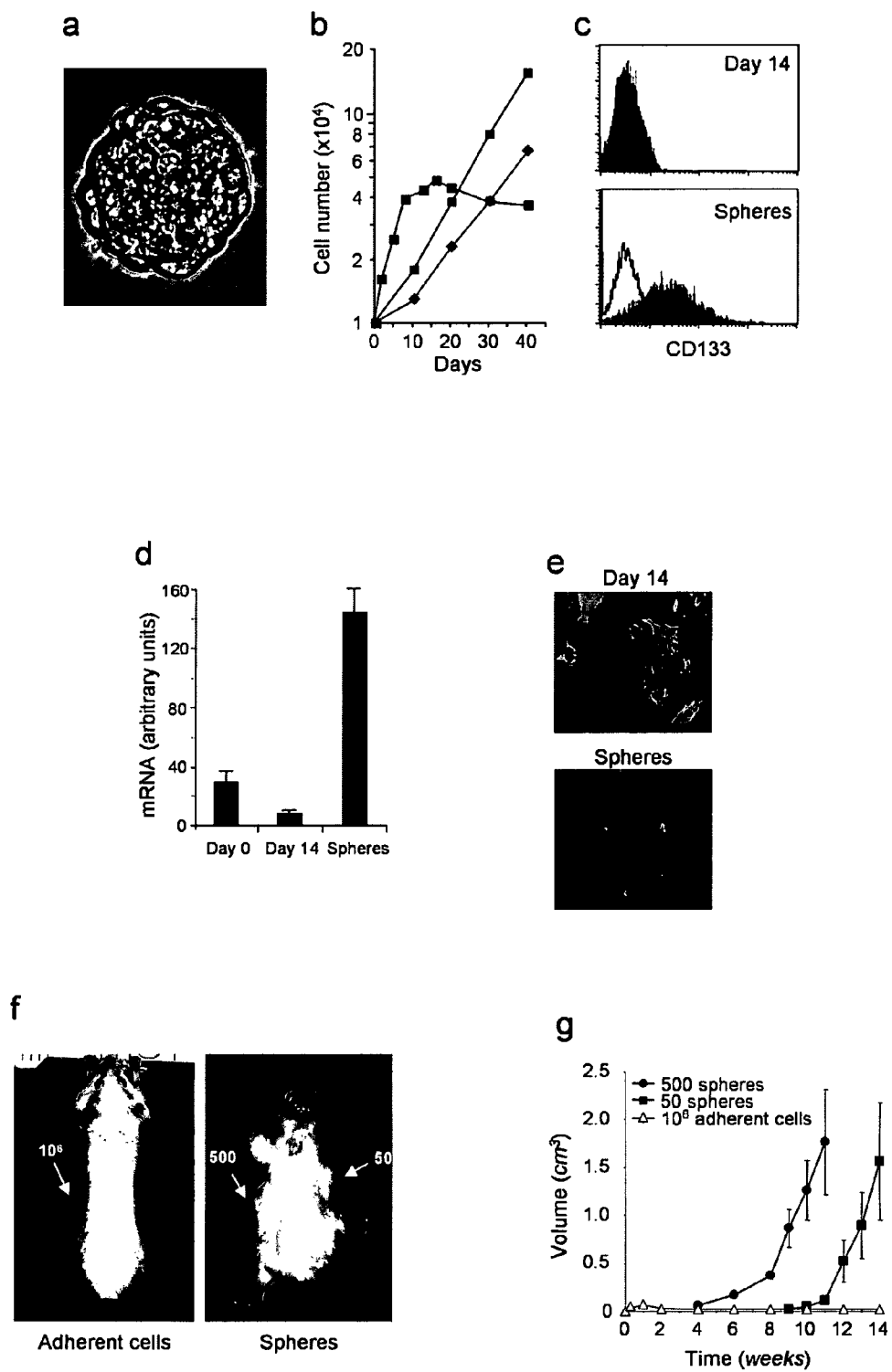
FIG. 2 shows that tumorigenic CD133+ colon cancer cells can be expanded in vitro as undifferentiated spheres. a, A typical colon cancer sphere obtained in serum-free medium containing EGF and FGF-2. b, Growth curve of colon sphere cells before passage 10 (red) or after passage 30 (black), as compared with the growth of primary colon cancer cells in standard medium with 10% serum (blue). c, d, Expression of CD133 by flow cytometry analysis (c) and real time PCR (d) in standard adherent primary colon cancer cultures at day 14 (Day 14), as compared with colon spheres (spheres) and freshly isolated colon cancer cells (Day 0). e, Immunofluorescence analysis of CK20 (green) in day 14 primary colon cancer cells and in colon cancer spheres. Nuclei are counterstained with Hoechst 33342 (blue). f, g, Tumorigenic potential of in vitro expanded CD133+ colon cancer spheres (Spheres) as compared with day 14 primary colon cancer cells from standard serum-driven cultures (Adherent cells). Injection sites of indicated number of cells and spheres in SCID mice are shown by arrows (f). Tumour volumes of mice injected with $10^6$ adherent cells from standard primary cultures, 50 spheres or 500 spheres (g). Data are mean±s.d. of 4 independent experiments in triplicate.

This standard culture of adherent cells did not allow the persistence of the CD133+ population, whose presence was essentially undetectable after 10 days of culture (FIG. 2c-d). As reported, the vast majority of cells obtained in this condition expressed CK20[18] (FIG. 2e). In contrast, cells grown as colon spheres maintained CD133 positivity and expressed negligible amounts of CK20 (FIG. 2c-e). The ability to grow exponentially and the absence of CK20 suggested that CD133+ colon spheres were clusters of primitive cancer cells. To investigate whether expanded CD133+ cells in tumour spheres maintained the tumorigenic potential, we injected subcutaneously in SCID mice 50 or 500 spheres and monitored weekly the formation of tumours. While $10^6$ differentiated primary colon cancer cells were not tumorigenic, the tumour spheres engrafted and generated tumours, which once formed grew rapidly and required animal sacrifice (FIG. 2f-g). Notably, injection of higher number of spheres resulted in faster appearance of the tumours without altering the cancer growth rate, which was independent of the number of transplanted spheres (FIG. 2g).

Figure 3:
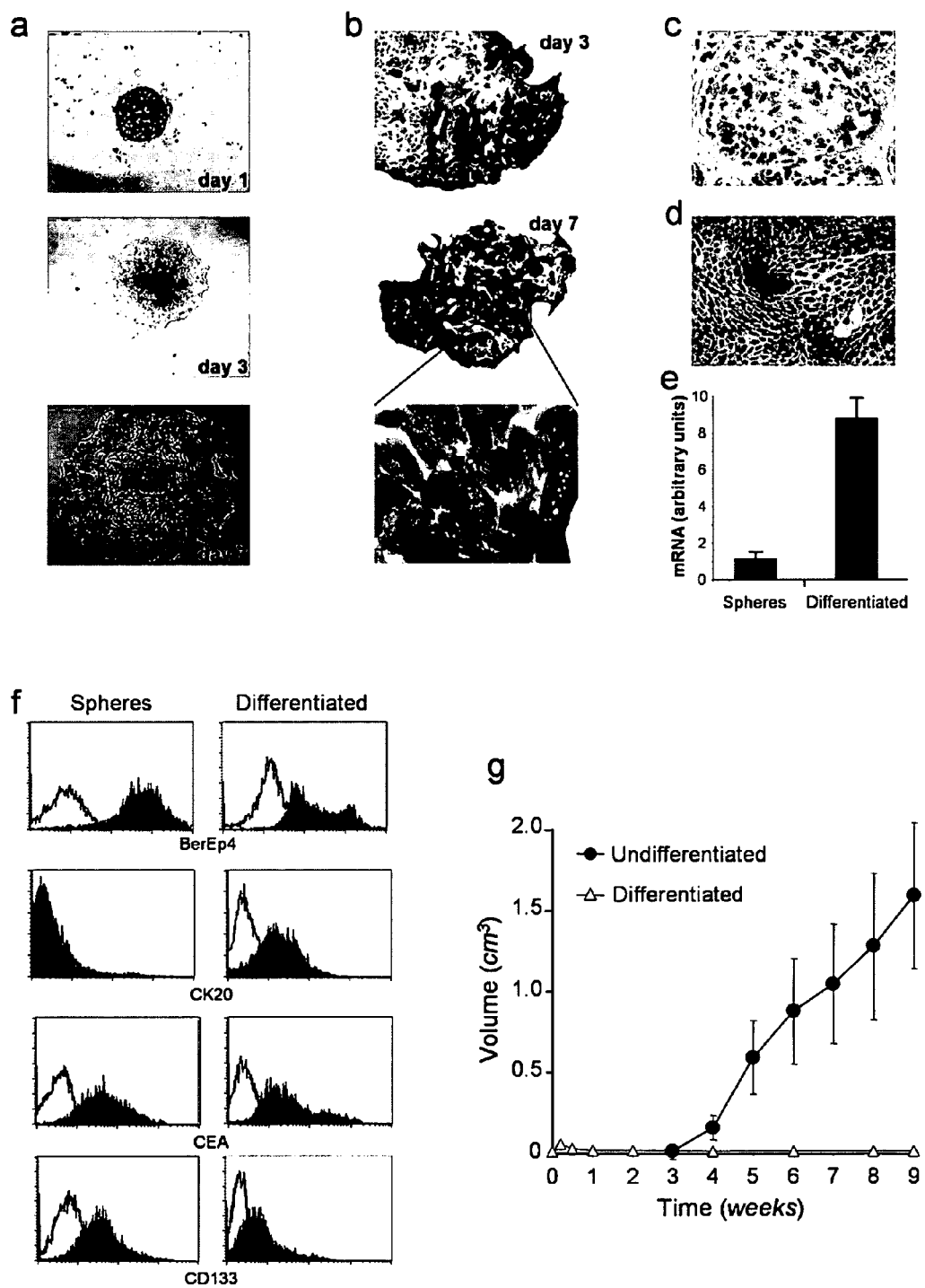
FIG. 3 shows that the tumorigenic potential of CD133+ colon cancer cells is lost upon differentiation. a, Microscopical analysis of colon cancer spheres cultivated in differentiative conditions for 1, 3 and 7 days. b, Immunocytochemical analysis of CK20 expression (brown) in differentiating colon cancer spheres. A higher magnification of the cells included in the red square is shown at the bottom. c, d, Immunocytochemical analysis of CDX2 expression (dark brown) in fibrin-included colon cancer spheres (c) and day 7 differentiated cells (d). e, Real time PCR analysis of CDX2 mRNA expression in colon cancer spheres and day 7 differentiated spheres. f, Flow cytometry analysis of colon cancer spheres and day 7 differentiated cells. Empty histograms represent isotype controls, grey histograms represent the specific binding for the indicated antigen. g, Tumorigenic potential of undifferentiated and differentiated CD133+ colon cancer cells derived by spheres. Tumour volumes of mice injected with $5 \times 10^5$ cells is shown. Data are mean±s.d. of 3 independent experiments with case #1, #3 and #7.

To determine the differentiation potential of these CD133+ cells, tumour spheres were cultivated without EGF and FGF-2 in the presence of 5% serum. After one day of culture, floating undifferentiated cells attached to the plastic, gradually migrating from tumour spheres and differentiating into large and adherent cells (FIG. 3a). Upon differentiation, colon cancer cells expressed CK20 and acquired a morphology closely resembling the major colon cancer cell population present in the original tumour (FIG. 3b). These differentiated cells expressed high levels of the caudal type homeobox transcription factor 2 (CDX2), a sensitive and specific marker for colorectal adenocarcinoma that was weakly expressed in colon spheres (FIG. 3c-e)[19,20]. Comparative flow cytometry analysis of colon cancer cells from undifferentiated and differentiated tumour spheres showed that all cells expressed Ber-EP4 and CEA, while CD133 was significantly downregulated upon differentiation (FIG. 3f). During the differentiation process, CD133+ cells lost their ability to transfer the tumour in immunocompromised mice (FIG. 3g and Table 3), suggesting that colon cancer initiating cells need to remain in an undifferentiated state in order to maintain the tumorigenic potential.

Thus, colon undifferentiated cancer cells can be cultured and expanded in vitro as colon spheres in proliferative serum-free medium containing growth factors. This property is common to neural and epithelial stem and progenitor cells, which grow as spherical clusters that in the presence of serum or extracellular matrix differentiate upon growth factor removal[15-17].

The possibility to obtain unlimited expansion of tumorigenic colon cancer cells could be exploited for more accurate preclinical studies provided that the expanded cells do not lose the ability to reproduce the original tumour. Although tumour cells may acquire genomic mutations after prolonged expansion, colon cancer spheres could be maintained in conditions of exponential growth for more than one year, without losing the ability to generate tumours. Tumour xenografts derived from colon spheres maintained in culture for one, six or twelve months closely reproduced the histological features of the original tumour, as indicated by hematoxylin-eosin staining and morphology analysis of tumour sections (FIG. 4a). Moreover, regardless of the duration of the in vitro expansion, tumours generated by colon spheres displayed a pattern of CDX2, β-catenin and CK20 identical to the primary tumour from which the cells have been derived (FIG. 4b), indicating that expanded CD133+ cells maintain their tumorigenic potential along with the ability to replicate the original tumour.

To investigate whether CD133+ colon cancer cells display long-term tumorigenic potential, we evaluated the ability of these cells to generate tumours after serial transplantations.

Figure 7:
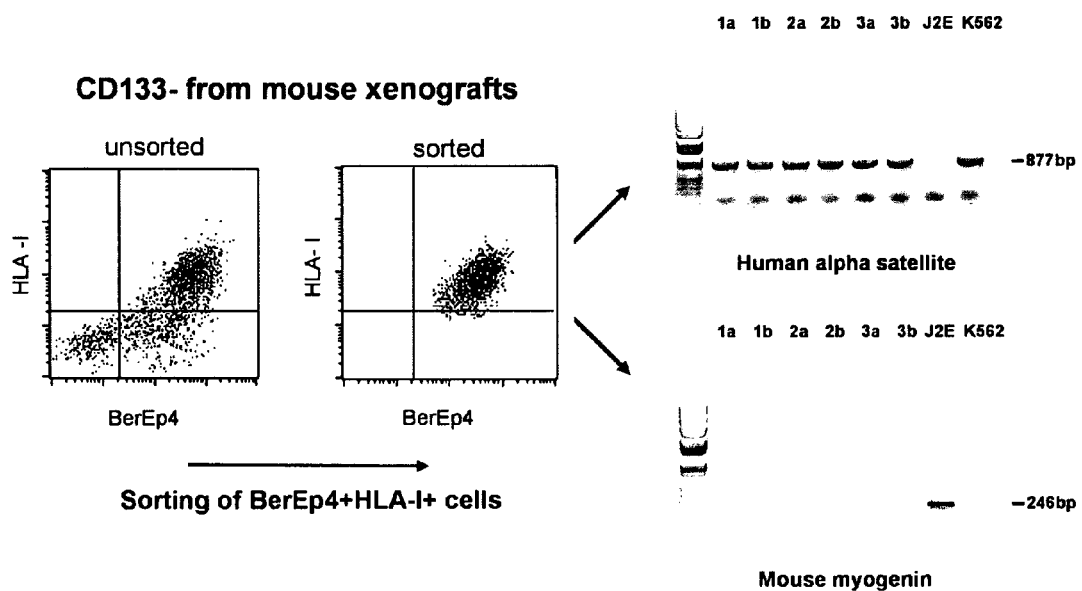
FIG. 7 shows that the CD133− population of mouse xenografts derived from CD133+ cells contain a considerable number of human cells. Flow cytometry analysis of HLA-I and BerEP4 in CD133− cells isolated from freshly dissociated xenografts before (unsorted) and after sorting of double positive cells (sorted). Genomic DNA was extracted from sorted cells and amplified for human alpha satellite (right, top) and mouse myogenin (right, bottom).

Tumour xenografts derived by the injection of freshly-isolated CD133+ cells were digested to isolate CD133+ and CD133− cells, which in turn were transplanted into secondary mice. Although the CD133− population contained a majority of human colon cancer cells (FIG. 7), only unseparated and CD133+ cells were tumorigenic, whereas CD133− cells were not able to transfer the tumour in secondary mice (FIG. 4c), confirming the data obtained with cells directly isolated from the human tumour. Moreover, CD133+ tumour spheres obtained from similar CD133+-derived primary xenografts were subsequently transplanted into secondary mice whose tumours were used as a new source of CD133+ cells to generate tertiary and then quaternary tumours (Table 3). During the in vivo passages, CD133+ cells did not lose their tumorigenic potential but, rather, they increased their aggressiveness, as indicated by the faster growth and increasing number of CD133+CK20− cells of newly generated tumours (FIG. 4d-e).

Accordingly, tumour spheres generated in vitro from these xenografts displayed an exponential growth that had the propensity to increase with serial xenografting (FIG. 4f). Thus, the CD133+ cell population resident in the colon tumour mass is able to generate serial xenografts showing a virtually unlimited growth potential.

Discussion

We have demonstrated that tumorigenic colon cells are included in the rare undifferentiated population that expresses CD133. This antigen is a 120 kDa five transmembrane domain glycoprotein expressed on normal primitive hematopoietic, endothelial, neural and epithelial cells[5-7]. In adult and juvenile brain tumours, CD133 is a marker for cancer initiating cells expressed by 6 to 29% of the total tumour population[4]. The determination of the cloning efficiency is currently not available for this tumorigenic colon cancer population, due to the limitation of the in vitro system and inability of single CD133+ cells to grow in clonogenic assays. However, the small number of CD133+ cells present in the colon cancer cell mass suggests that a significant proportion of these cells is tumorigenic and able to contribute to disease progression.

Our data are in line with the cancer stem cell hypothesis that suggest that tumours are generated and maintained by a small subset of undifferentiated cells able to self renew and differentiate into the bulk tumour population[21]. As in other cancer types, such as leukaemia[2], breast[14] and brain cancer[4], early progenitor or stem cells seem the target of oncogenic transformation in colon cancer. It is likely that these undifferentiated cells undergo symmetric and asymmetric divisions in vivo, resulting in the expansion of the tumorigenic cell compartment, while producing a progeny of more differentiated cells that constitute the prevalent population of the tumour cell mass[22].

The disclosure of all references cited herein is hereby incorporated by reference, unless otherwise apparent.

REFERENCES FOR METHODS AND DESCRIPTION

1. Jemal, A. et al. Cancer statistics, 2006. *CA Cancer J Clin* 56, 106-30 (2006).
2. Bonnet, D. & Dick, J. E. Human acute myeloid leukemia is organized as a hierarchy that originates from a primitive hematopoietic cell. *Nat Med* 3, 730-7 (1997).
3. Pardal, R., Clarke, M. F. & Morrison, S. J. Applying the principles of stem-cell biology to cancer. *Nat Rev Cancer* 3, 895-902 (2003).
4. Singh, S. K. et al. Identification of human brain tumour initiating cells. *Nature* 432, 396-401 (2004).
5. Uchida, N. et al. Direct isolation of human central nervous system stem cells. *Proc Natl Acad Sci USA* 97, 14720-5 (2000).
6. Yin, A. H. et al. AC133, a novel marker for human hematopoietic stem and progenitor cells. *Blood* 90, 5002-12 (1997).
7. Salven, P., Mustjoki, S., Alitalo, R., Alitalo, K. & Rafii, S. VEGFR-3 and CD133 identify a population of CD34+ lymphatic/vascular endothelial precursor cells. *Blood* 101, 168-72 (2003).
8. Moll, R. Cytokeratins as markers of differentiation in the diagnosis of epithelial tumours. *Subcell Biochem* 31, 205-62 (1998).
9. Davidson, B. et al. Detection of malignant epithelial cells in effusions using flow cytometric immunophenotyping: an analysis of 92 cases. *Am J Clin Pathol* 118, 85-92 (2002).
10. Sheahan, K. et al. Differential reactivities of carcinoembryonic antigen (CEA) and CEA-related monoclonal and polyclonal antibodies in common epithelial malignancies. *Am J Clin Pathol* 94, 157-64 (1990).
11. Powell, S. M. et al. APC mutations occur early during colorectal tumourigenesis. *Nature* 359, 235-7 (1992).
12. Rodrigues, N. R. et al. p53 mutations in colorectal cancer. *Proc Natl Acad Sci U S A* 87, 7555-9 (1990).
13. Jessup, J. M. et al. Growth potential of human colorectal carcinomas in nude mice: association with the preoperative serum concentration of carcinoembryonic antigen in patients. *Cancer Res* 48, 1689-92 (1988).
14. Al-Hajj, M., Wicha, M. S., Benito-Hernandez, A., Morrison, S. J. & Clarke, M. F. Prospective identification of tumorigenic breast cancer cells. *Proc Natl Acad Sci U S A* 100, 3983-8 (2003).
15. Vescovi, A. L. et al. Isolation and cloning of multipotential stem cells from the embryonic human CNS and establishment of transplantable human neural stem cell lines by epigenetic stimulation. *Exp Neurol* 156, 71-83 (1999).
16. Dontu, G. et al. In vitro propagation and transcriptional profiling of human mammary stem/progenitor cells. *Genes Dev* 17, 1253-70 (2003).
17. Singh, S. K. et al. Identification of a cancer stem cell in human brain tumours. *Cancer Res* 63, 5821-8 (2003).
18. Chu, P., Wu, E. & Weiss, L. M. Cytokeratin 7 and cytokeratin 20 expression in epithelial neoplasms: a survey of 435 cases. *Mod Pathol* 13, 962-72 (2000).
19. Ee, H. C., Erler, T., Bhathal, P. S., Young, G. P. & James, R. J. Cdx-2 homeodomain protein expression in human and rat colorectal adenoma and carcinoma. *Am J Pathol* 147, 586-92 (1995).
20. Witek, M. E. et al. The putative tumour suppressor Cdx2 is overexpressed by human colorectal adenocarcinomas. *Clin Cancer Res* 11, 8549-56 (2005).
21. Wang, J. C. & Dick, J. E. Cancer stem cells: lessons from leukemia. *Trends Cell Biol* 15, 494-501 (2005).
22. Clevers, H. Stem cells, asymmetric division and cancer. *Nat Genet* 37, 1027-8 (2005).

REFERENCES FOR SUPPLEMENTARY METHODS

1. Gannon, J. V. et al. Activating mutations in p53 produce a common conformational effect. A monoclonal antibody specific for the mutant form. *EMBO J* 9, 1595-602 (1990).
2. Prosser, J. et al. APC mutation analysis by chemical cleavage of mismatch and a protein truncation assay in familial adenomatous polyposis. *Br J Cancer* 70, 841-6 (1994).
3. Norheim Andersen, S. et al. Germline and somatic mutations in exon 15 of the APC gene and K-ras mutations in duodenal adenomas in patients with familial adenomatous polyposis. *Scand J Gastroenterol* 34, 611-7 (1999).

TABLE 1

| CASE | AGE | SEX | COLON SITE | GRADE | TNM | Dukes |
|---|---|---|---|---|---|---|
| 1 | 68 | M | Sigma | G3 | IIIB | C |
| 2 | 41 | M | Left | G3 | IIIC | C |
| 3 | 69 | F | Sigma | G2 | IV | D |
| 4 | 66 | F | Left | G2 | I | A |
| 5 | 67 | M | Sigma | G2 | IIIC | C |
| 6 | 76 | M | Right | G2 | IIIB | C |
| 7 | 68 | M | Sigma | G2 | IIIB | C |
| 8 | 74 | M | Sigma | G3 | I | A |
| 9 | 58 | M | Sigma | G2 | I | A |
| 10 | 66 | F | Right | G2 | IIA | B |
| 11 | 79 | F | Sigma | G2 | I | A |
| 12 | 53 | M | Right | G2 | IIIC | C |
| 13 | 70 | F | Sigma | G2 | IIA | B |
| 14 | 73 | F | Right | G2 | IIA | B |
| 15 | 68 | M | Left | G2 | IIIC | C |
| 16 | 51 | M | Sigma | G2 | IIA | B |
| 17 | 53 | M | Left | G2 | I | A |
| 18 | 76 | F | Sigma | G2 | IIA | B |

TABLE 2

| | | Number of cells injected | | | | | | |
| | | Freshly dissociated | | | | After in vivo passaging | | |
| CASE | CD133 | CD133+ | CD133− | CD133−CEA+ | Unseparated | Unseparated | CD133+ | CD133− |
|---|---|---|---|---|---|---|---|---|
| 1 | 2.4% | 100,000 (2/2) | 100,000 (0/2) | | 1,000,000 (2/4) | | | |
| | | 10,000 (1/2) | 10,000 (0/2) | | | | | |
| | | 3,000 (2/2) | 5,000 (0/2) | | | | | |

TABLE 2-continued

| | | Number of cells injected | | | | | | |
|---|---|---|---|---|---|---|---|---|
| | | Freshly dissociated | | | | After in vivo passaging | | |
| CASE | CD133 | CD133+ | CD133− | CD133−CEA+ | Unseparated | Unseparated | CD133+ | CD133− |
| 2 | 2% | 10,000 (0/2)<br>5,000 (0/2)<br>3,000 (0/2) | 100,000 (0/2)<br>10,000 (0/2)<br>5,000 (0/2) | | 1,000,000 (0/4) | | | |
| 3 | 2.5% | 10,000 (2/2)<br>5,000 (2/2)<br>3,000 (2/2) | 100,000 (0/2)<br>10,000 (0/2)<br>5,000 (0/2) | | 1,000,000 (3/4) | | | |
| 4 | 1.7% | 10,000 (0/2)<br>5,000 (0/2)<br>3,000 (0/2) | 100,000 (0/2)<br>10,000 (0/2)<br>5,000 (0/2) | | 1,000,000 (0/4) | | | |
| 5 | 1.4% | 10,000 (2/2)<br>5,000 (1/2)<br>3,000 (1/2) | 100,000 (0/2)<br>10,000 (0/2)<br>5,000 (0/2) | | 1,000,000 (0/4) | | | |
| 6 | 2.4% | 10,000 (1/2)<br>5,000 (2/2)<br>3,000 (2/2) | 100,000 (0/2)<br>10,000 (0/2) | | 1,000,000 (2/4) | | | |
| 7 | 1.8% | 10,000 (2/2)<br>5,000 (2/2)<br>3,000 (2/2) | 100,000 (0/2)<br>10,000 (0/2) | | 1,000,000 (3/4) | | | |
| 8 | 0.7% | 5,000 (0/2)<br>3,000 (0/2)<br>1,500 (0/2) | 100,000 (0/2)<br>10,000 (0/2) | | 1,000,000 (0/4) | | | |
| 9 | 2.4% | 5,000 (0/2)<br>3,000 (0/2)<br>1,500 (0/2) | 100,000 (0/2)<br>10,000 (0/2) | | 1,000,000 (0/4) | | | |
| 10 | 0.7% | 5,000 (2/2)<br>3,000 (1/2)<br>1,500 (1/2) | 100,000 (0/2)<br>10,000 (0/2) | | 1,000,000 (1/4) | | | |
| 13 | 2.6% | 10,000 (1/2)<br>5,000 (2/2)<br>3,000 (1/2) | | 10,000 (0/2)<br>100,000 (0/2) | 1,000,000 (1/4) | | | |
| 14 | 4.1% | 10,000 (0/2)<br>5,000 (0/2)<br>3,000 (0/2) | | 10,000 (0/2)<br>100,000 (0/2) | 1,000,000 (0/4) | | | |
| 15 | 2.7% | 10,000 (2/2)<br>5,000 (2/2)<br>3,000 (2/2) | | 10,000 (0/2)<br>100,000 (0/2) | 1,000,000 (2/4) | 100,000 (2/2) | 100,000 (0/2) | 100,000 (2/2) |
| 16 | 6.1% | 10,000 (2/2)<br>5,000 (2/2)<br>3,000 (2/2) | | 10,000 (0/2)<br>100,000 (0/2) | 1,000,000 (4/4) | 100,000 (2/2) | 100,000 (0/2) | 100,000 (2/2) |
| 17 | 1.7% | 10,000 (0/2)<br>5,000 (0/2)<br>3,000 (0/2) | | 10,000 (0/2)<br>100,000 (0/2) | 1,000,000 (0/4) | | | |
| 18 | 4.6% | 10,000 (2/2)<br>5,000 (1/2)<br>3,000 (2/2) | | 10,000 (0/2)<br>100,000 (0/2) | 1,000,000 (1/4) | | | |

TABLE 3

| | Long term cultures | | | Number of spheres injected | Xenografts | | | | |
|---|---|---|---|---|---|---|---|---|---|
| | | | | | Number of cells injected | | Number of spheres injected | | |
| CASE | Total | CD133+ | CD133− | injected | Undifferentiated | Differentiated | Secondary | Tertiary | Quaternary |
| 1 | Yes | — | — | 50 (3/3); 500 (3/3) | $5 \times 10^5$ (2/2)<br>$5 \times 10^5$ (2/2) | $5 \times 10^5$ (0/2)<br>$5 \times 10^5$ (0/2) | 50 (2/2)<br>50 (2/2) | 50 (2/2)<br>50 (2/2) | 50 (2/2)<br>50 (2/2) |
| 2 | No | No | No | | | | | | |
| 3 | Yes | Yes | No | 50 (3/3); 500 (3/3) | $5 \times 10^5$ (2/2)<br>$5 \times 10^5$ (2/2) | $5 \times 10^5$ (0/2)<br>$5 \times 10^5$ (0/2) | | | |
| 4 | No | No | No | | | | | | |
| 5 | No | No | No | | | | | | |
| 6 | No | No | No | | | | | | |
| 7 | Yes | Yes | No | 50 (2/3); 500 (3/3) | $5 \times 10^5$ (2/2)<br>$5 \times 10^5$ (2/2) | $5 \times 10^5$ (0/2)<br>$5 \times 10^5$ (0/2) | 50 (2/2) | 50 (2/2) | 50 (2/2) |
| 8 | No | No | No | | | | | | |
| 9 | No | No | — | | | | | | |
| 10 | Yes | No | — | 50 (3/3); 500 (2/3) | | | | | |
| 11 | No | No | — | | | | | | |
| 12 | No | No | — | | | | | | |

Example 2

Other Cancers

Similar experiments were repeated for other cancer types in the digestive system, including pancreatic cancer. The protocols used in Colon cancer were repeated as appropriate.

Recent publications in this area include Li et al (Cancer Res. 2007 Feb. 1; 67(3):1030-7. *Identification of pancreatic cancer stem cells*, Li C, Heidt D G, Dalerba P, Burant C F, Zhang L, Adsay V, Wicha M, Clarke M F, Simeone D M) and Ma et al (Gastroenterology. 2007 June; 132(7):2542-2556 17570225 *Identification and Characterization of Tumourigenic Liver Cancer Stem/Progenitor Cells*, Stephanie Ma, Kwok-Wah Cha, Liang Hu, Terence Kin-Wah Lee, Jana Yim-Hung Wo, Irene Oi-Lin Ng, Bo-Jian Zheng, Xin-Yuan Guan).

Figure 8:
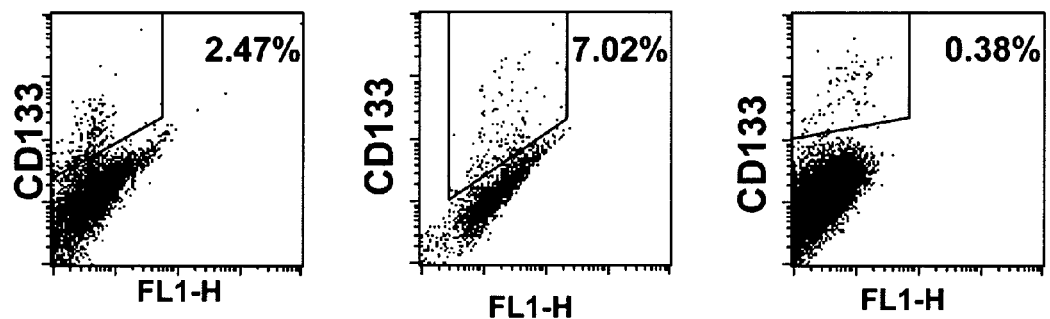
FIG. 8A shows that pancreatic carcinomas express CD133 in a subset of tumor cells. Flow cytometry analysis of CD133 expression in freshly dissociated tumours samples from three different patients.
FIG. 8B shows that tumourigenic cells in pancreatic carcinomas are included in the CD133+ population. Freshly isolated CD133+, CD133− and unseparated (total) pancreatic tumor cells were resuspended in Matrigel and injected subcutaneously in SCID mice. Data represent mean±s.d. of three independent experiments in duplicate using the indicated number of cells from three different patients.
Figure 8:
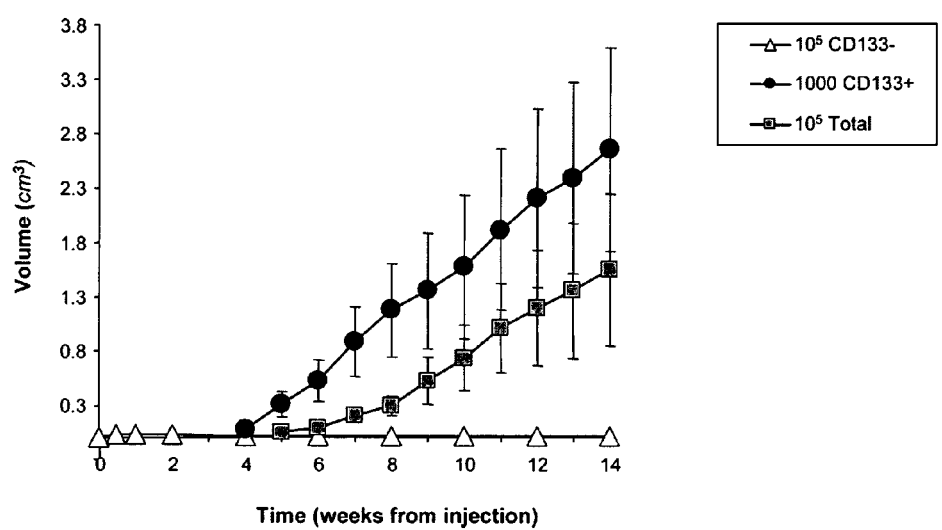
Figure 9:
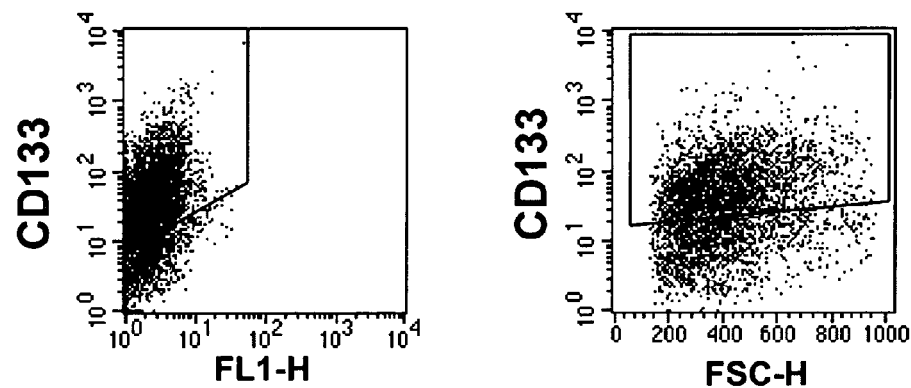
FIGS. 9A-9B show that pancreatic tumor spheres express CD133 and are tumourigenic in immunocompromised mice.
Figure 9:
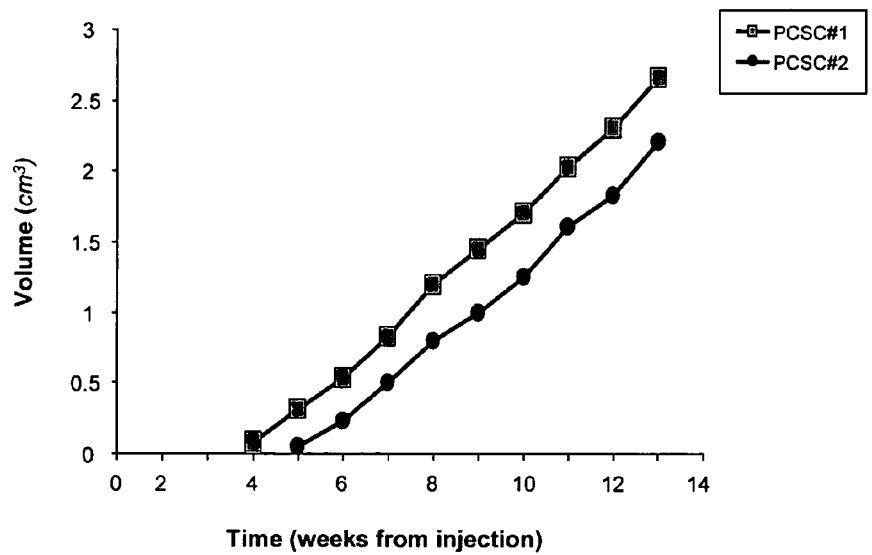

The results of experiments done in respect of pancreatic cancer confirm that CD133+ are markers for pancreatic cancer and that tumour spheres containing CD133+ cells are tumourigenic in immunocompromised mice. These findings are shown in FIGS. 8 and 9: FIG. 8A shows that pancreatic carcinomas express CD133 in a subset of tumor cells. Flow cytometry analysis of CD133 expression in freshly dissociated tumours samples from three different patients.

FIG. 8B shows that tumourigenic cells in pancreatic carcinomas are included in the CD133+ population. Freshly isolated CD133+, CD133− and unseparated (total) pancreatic tumor cells were resuspended in Matrigel and injected subcutaneously in SCID mice. Data represent mean±s.d. of three independent experiments in duplicate using the indicated number of cells from three different patients.

FIGS. 9A-9B shows that pancreatic tumor spheres express CD133 and are tumourigenic in immunocompromised mice. FIG. 9A: Representative CD133 expression of tumor spheres from pancreatic carcinomas grown in serum-free medium in the presence of EGF and basic FGF. FIG. 9B: Tumourigenic activity of 50 spheres resuspended in Matrigel and injected subcutaneously in SCID mice. Data represent a typical experiment of three, using two pancreatic cancer stem cell lines obtained from two different patients.

Example 3

Reproduction of Cancer Metastasis in Mice

Further work was carried out in respect of introducing tumour spheres containing CD133+ cells into immunocompromised mice. The introduction of CD133+ cells, originally isolated from colon cancer, as xenografts into the lungs of immunocompromised mice, led to the formation of colon-cancer metastases in the lung tissue. The same was also found in the spleen and peritoneum.

This is particularly useful in the provision of in vivo mammalian models, such as mice, with xenograft metastases and the study of such cancers.

Also of note is that the CD133+ cells can be introduced both at the desired site by orthotopic injection, for instance, or by introduction into the blood, as was the case for the lung metastases.

Method:

A representative of multiple independent experiments is shown. Tumour formation was observed after 4-12 weeks of injection. The time required for tumour growth was related to the number of cells injected. A range of 500 to 10 million CD133+ cells was used.

Figure 10:
FIGS. 10A-10D show that cultivated CD133+ cancer stem cells reproduce colon cancer metastasis in immunocompromised mice.
Figure 10:
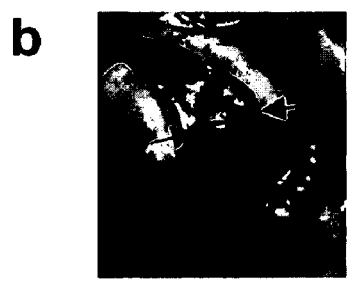
Figure 10:
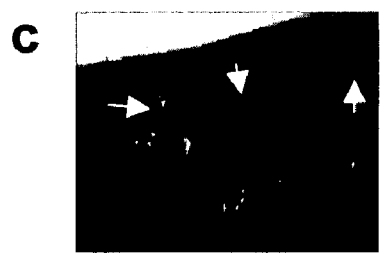
Figure 10:
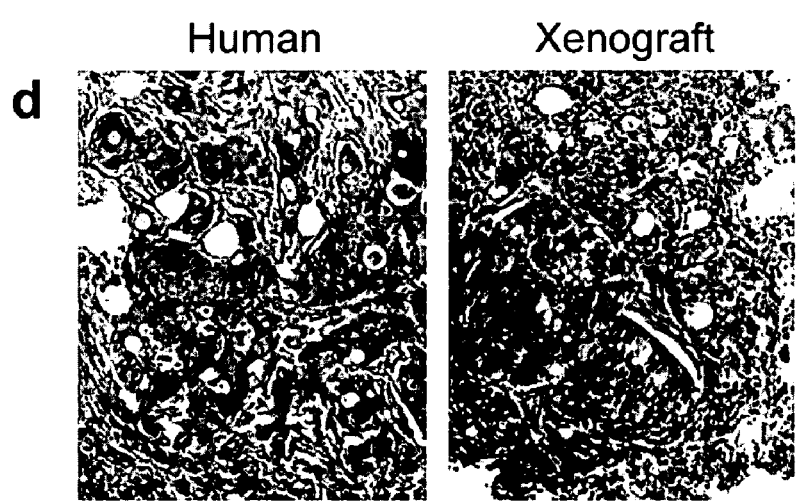

Results:

The results are shown in FIG. 10:

FIGS. 10A-10D show that cultivated CD133+ cancer stem cells reproduce colon cancer metastasis in immunocompromised mice. FIG. 10A: Colon cancer xenografts reproducing lung cancer metastases are obtained by injection of CD133+ cells either in the tail vein or orthotopically in SCID mice. Arrows indicate colon cancer-like metastases in the lung parenchyma.

FIG. 10B: Colon cancer xenografts reproducing spleen metastases are obtained by orthotopic injection of CD133+ cells. Arrows indicate colon cancer-like metastases in the spleen parenchyma.

FIG. 10C: Colon cancer xenografts reproducing intraperitoneal metastases are obtained by orthotopic injection of CD133+ cells. Arrows indicate colon cancer-like metastases in the mouse peritoneum.

FIG. 10D: Hematoxylin-eosin analysis showed a similar histological patterns between original tumor (human) and the mouse xenografts obtained after injection of CD133+ colon cancer cells.

Example 4

Suitable Conditions For Cultivating CD133+ Cells

An example of suitable conditions for cultivating CD133+ gastrointestinal tumour cells is described below.

Tumor samples are washed several time with phosphate buffer saline (PBS) at room temperature and incubated overnight at 4° C. in DMEM-F12 containing 25 units/ml of penicillin, 25 mg/ml of streptomycin and 10 mg/ml amphotericin B. The day after, samples are subjected to mechanical dissociation followed by enzymatic dissociation in DMEM-F12 containing 1.5 mg/ml of collagenase I, 20 mg/ml of DNase 1 and 500 mg/ml of hyaluronidase, for about 30-60 min depending on sample size. At the end of the enzymatic digestion, cell suspension is filtered by using a 100 mm nylon cell strainer. The resulting cancer cells are cultured in NS-A basal serum free medium containing 2 mM L-glutamine, 0.6% glucose, 9.6 mg/ml putrescine, 6.3 ng/ml progesterone, 5.2 ng/ml sodium selenite, 4 mg/ml heparin sodium salt, 100 ng/ml hydrocortisone, 0.025 mg/ml insulin, 0.1 mg/ml apotrasferrin and supplemented with 20 ng/ml EGF, 10 ng/ml bFGF and 10 ng/ml IGF-I. Cells are preferably cultivated in low-adherence culture flask in serum-free conditions. However, serum, preferably from foetal calf, may be added during the first days of cultures.

Cells grow preferentially as non-adherent tumor spheres. However, they may grow as adherent or partially adherent tumor clusters. During each passage, spheres are mechanically or chemically reduced in single cells or in small clusters to allow further growth.

The invention claimed is:

1. A method for selecting a potential therapeutic agent for use in the treatment of CD133+ tumor cells, said method comprising the steps of:
  (a) providing a sample of fresh digestive system tumor tissue or gastrointestinal tumor tissue comprising undifferentiated tumorigenic CD133+ cells;
  (b) selectively culturing and expanding the undifferentiated tumorigenic CD133+ cells as spherical clusters in serum-free medium comprising epidermal growth factor and fibroblast growth factor-2;
  (c) contacting the cultured undifferentiated tumorigenic CD133+ digestive system cells or the cultured undifferentiated tumorigenic CD133+ gastrointestinal tumor cells with a test compound;
  (d) determining the number of CD133+ cells in the culture contacted with the test agent;
  (e) detecting CD133+ cells in a culture not treated with the test agent whereby a potential therapeutic agent for use in the treatment of CD133+ tumor cells is identified when the number of undifferentiated tumorigenic CD133+ cells are reduced in the culture-treated with the test compound as compared to the number of undifferentiated tumorigenic CD133+ cells in the culture not treated with the test compound.

2. The method of claim 1, wherein the tumor tissue is from the gastrointestinal tract.

3. The method of claim 1, wherein the sample is taken from the mouth, stomach, small intestine, colon or rectum or wherein the cancer is oral, esophageal, stomach, ileac, bowel or colorectal cancer.

4. The method of claim 1, wherein the spherical clusters of cells are CD133+ colon carcinoma cells.

* * * * *